United States Patent [19]
Malik et al.

[11] Patent Number: 5,637,772
[45] Date of Patent: Jun. 10, 1997

[54] FLUORINATED DIAMINES AND POLYMERS FORMED THEREFROM

[75] Inventors: Aslam A. Malik, Cameron Park; Roland P. Carlson, Davis, both of Calif.

[73] Assignee: Aerojet General Corporation, Rancho Cordova, Calif.

[21] Appl. No.: 532,382

[22] Filed: Sep. 22, 1995

[51] Int. Cl.$^6$ .................................................. C07C 211/10
[52] U.S. Cl. .......................... 564/505; 564/503; 564/504
[58] Field of Search ........................... 564/505, 504, 564/503, 510

[56] References Cited

U.S. PATENT DOCUMENTS

| | | | |
|---|---|---|---|
| 3,564,059 | 2/1971 | Sianesi et al. | 260/594 |
| 3,810,874 | 5/1974 | Mitsch et al. | 260/75 H |
| 4,080,319 | 3/1978 | Caporiccio et al. | 528/183 |
| 4,085,137 | 4/1978 | Mitsch et al. | 260/561 HL |
| 4,165,338 | 8/1979 | Katsushima et al. | 260/584 R |
| 4,683,289 | 7/1987 | Ohsaka et al. | 528/402 |
| 4,788,339 | 11/1988 | Moore et al. | 564/457 |
| 4,814,372 | 3/1989 | Caporiccio et al. | 528/485 |
| 5,097,048 | 3/1992 | Falk et al. | 549/511 |
| 5,120,459 | 6/1992 | Kalota et al. | 252/54 |
| 5,145,999 | 9/1992 | Auman et al. | 564/442 |
| 5,175,367 | 12/1992 | Feiring | 564/309 |
| 5,196,595 | 3/1993 | Navarrini et al. | 564/504 |
| 5,286,825 | 2/1994 | Anton et al. | 526/247 |
| 5,288,908 | 2/1994 | Lau et al. | 564/335 |
| 5,322,917 | 6/1994 | Auman et al. | 528/185 |
| 5,324,813 | 6/1994 | Hougham et al. | 528/353 |
| 5,491,261 | 2/1996 | Haniff et al. | 562/582 |

*Primary Examiner*—Brian M. Burn
*Attorney, Agent, or Firm*—Townsend and Townsend and Crew LLP

[57] ABSTRACT

The present invention provides fluorinated diamines and polymers formed therefrom, such as polyureas, polyurethane ureas, polyamides, polyimides, etc. The fluorinated diamines of the present invention are highly nucleophilic and are structured to provide polymeric materials having optimum surface properties. In the fluorinated diamines of the present invention, the end groups are primary amino groups which are substantially removed from the perfluoroalkyl groups. Moreover, the fluorine is present in the side chains which allows the fluorocarbon segments to migrate to the polymer/air interface, thereby providing polymer surfaces with high fluorine concentrations. As such, the polymers formed from the fluorinated diamines of the present invention have a variety of commercial applications as stain and oil resistant coatings, fouling release coatings, encapsulants for electrical devices, curing agents for epoxies, etc.

15 Claims, No Drawings

FLUORINATED DIAMINES AND POLYMERS FORMED THEREFROM

FIELD OF THE INVENTION

The present invention relates, in general, to fluorinated diamines and to polymers formed therefrom, such as polyureas, polyurethane ureas, polyamides, polyimides, etc. The fluorinated diamines of the present invention are highly nucleophilic and are structured to provide polymeric materials having optimal surface properties. In the fluorinated diamines of the present invention, the end groups are primary amino groups which are substantially removed from the perfluoroalkyl groups. Moreover, in the fluorinated diamines of the present invention, the fluorine is present in the side chains which allows the fluorocarbon segments to migrate to the polymer/air interface, thereby providing polymer surfaces with high fluorine concentrations. As such, the polymers formed from the fluorinated diamines of the present invention have a variety of commercial applications as stain and oil resistant coatings, fouling release coatings, encapsulants for electrical devices, curing agents for epoxies, etc.

STATEMENT OF GOVERNMENT INTEREST

This invention was made with Government support pursuant to Contract No. N0014-93-C-0068 awarded by the Department of the Navy. The Government has certain rights in this invention.

BACKGROUND OF THE INVENTION

Diamines, i.e., compounds which contain two primary amino ($—NH_2$) groups, constitute an important class of organic monomers. Diamines are particularly important because the two primary amino groups can be reacted with a variety of electrophiles to prepare polymers such as polyureas, polyamides and polyimides. In fact, one of the most commercially important polymers, i.e., "Nylon 66," is prepared from the reaction of hexamethylene diamine with adipoyl chloride. Moreover, due to the higher reactivity of the amino group as compared to the hydroxy group, diamines are finding increased use in commercial processes such as reaction injection molding (RIM).

Fluorinated diamines, in particular, are important because they have certain properties that make them valuable for a variety of applications. Fluorocarbon segments are generally incorporated into a polymer matrix to impart favorable dielectric, water-repellency, thermal, soil release and fouling release properties. Moreover, incorporation of fluorine also lowers the coefficient of friction and refractive index of the polymer system. These properties make fluorinated materials useful for diverse applications ranging from non-stick frying pans to water repellant clothing to drag-reducing coatings. Although the hydrocarbon analogs of telechelic diamines are well known, very few fluorinated diamines having useful properties are known to date.

Perfluorinated diamines, i.e., $H_2N(CF_2)_nNH_2$, are known, but they are unstable and readily eliminate hydrofluoric acid to form dinitriles. Due to the instability of these materials, no attempts have been made to isolate these diamines, or to incorporate them into a polymer matrix. Fluorinated diamines in which the amine functionality is separated from the fluorinated segment by one intervening methylene group are also known. Such fluorinated diamines have been prepared by the hydrogenation of the corresponding dinitrile derivatives (see, e.g., U.S. Pat. No. 2,515,246 issued to E. T. McBee and P. A. Wiseman (1950)), or by a three-step process from the corresponding fluoroalcohols T. F. Bell and R. N. Henrie, *OPPI Briefs*, 21(2): 245 (1989); and U.S. Pat. No. 4,020,176 issued to R. B. Greenwald (1977)). The use of these diamines in the synthesis of polymers, however, has been somewhat limited due to their low nucleophilicity, resulting primarily from the presence of a strongly electron-withdrawing perfluoroalkyl group on the neighboring carbon atom.

Synthesis of fluorinated diamines in which the amine functionality is separated from the fluorinated segment by two intervening methylene groups, i.e., $NH_2$—$CH_2CH_2$—$(CF_2)_n$—$CH_2CH_2$—$NH_2$, was recently described by Malik, et al., (see, *J. Org. Chem.*, 56: 3043 (1991)). These diamines were prepared by a three-step process involving free radical addition of perfluoroalkyl iodide to ethylene, displacement of the iodo groups with azide, and reduction of the diazide to diamine. Although these compounds are more reactive than fluorinated diamine analogs with one intervening methylene group, their reactivity is still much lower than that of the hydrocarbon analogs.

One of the major applications of specialty fluoropolymers is in the area of surface coatings. In order to prepare polymers with good surface properties, it is important to have fluorine in the side chain and not in the polymer backbone. (See, e.g., Hopken, J. and M. Moeller, *Macromolecules*, 25: 1461 (1992); Zisman, W. A., "Contact Angle, Wettability and Adhesion," *Advances in Chemistry Series*, American Chemical Society, vol. 43 (1964); and Kobayashi, H. and M. J. Owen, *Macromolecules*, 22: 2951 (1989)). When the currently available fluorinated diamines are incorporated into a polymer matrix, the fluorinated segments are buried in the bulk with the rest of the backbone, which contains polar groups such as urethane and urea linkages. Unfortunately, the presence of these polar groups increases the surface energy of the coatings and give materials with poor surface properties.

In view of the foregoing, there remains a need in the art for fluorinated diamines which overcome the disadvantages associated with the currently available fluorinated diamines. Quite surprisingly, the present invention remedies this need by providing such fluorinated diamines.

SUMMARY OF THE INVENTION

The present invention provides fluorinated diamines which are highly nucleophilic and which are structured to provide polymeric materials having optimal surface properties. In the fluorinated diamines of the present invention, the end groups are primary amino groups which are substantially removed from the electron-withdrawing perfluoroalkyl groups. Moreover, the fluorine is present in the side chains which allows the fluorocarbon segments to migrate to the polymer/air interface, thereby providing polymer surfaces with high fluorine concentrations. In addition, the fluorinated diamines of the present invention are miscible with highly fluorinated materials. This is a major advantage since the commercially available diamines (e.g., aliphatic diamines and aromatic diamines) are not miscible with fluorinated monomers. As a result, the fluorinated diamines of the present invention can be advantageously used to form fluorinated polymers having optimal surface properties. Polymers which can be formed using the fluorinated diamines of the present invention include, but not limited to, polyureas, polyurethane urea elastomers, polyamides, polyimides, epoxies etc.

As such, in one aspect of the present invention, a fluorinated diamine is provided, the fluorinated diamine having the general formula:

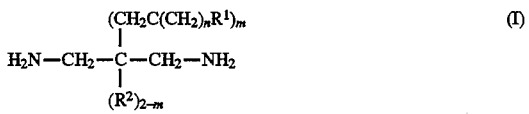

(I)

In Formula I, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, lower alkyls having from 1 to 4 carbon atoms. X is a functional group including, but not limited to, a valence bond —NR—, —O—, —S—, —$SO_2$— and —N(R)$SO_2$—. The index "m" represents an integer having a value of 1 or 2. The index "n" represents an integer having a value ranging from 1 to about 10.

In another aspect of the present invention, a fluorinated polyurea is provided, the fluorinated polyurea having the following general formula:

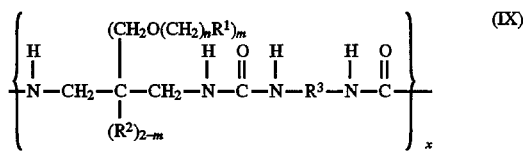

(IX)

In Formula IX, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, lower alkyls having from 1 to 4 carbon atoms. $R^3$ is a functional group including, but not limited to, alkyl and aryl radicals. The index "m" represents an integer having a value of 1 or 2; the index "n" represents an integer having a value ranging from 1 to about 10; and the index "x" is an integer having a value ranging from 5 to about 250.

The fluorinated polyureas of Formula IX exhibit a wide variety of useful properties including, but not limited to, the following: hydrophobic properties, low surface energies, low dielectric constants, high abrasion resistance and tear strength, low coefficients of friction, high adhesion and low refractive indices. Combinations of these properties make the fluorinated polyureas of the present invention extremely attractive for a variety of applications including, but not limited to, anti-fouling (release) coatings, ice release coatings, corrosion resistant coatings, automotive top coats (e.g., car wax), oil/soil resistant coatings, seals and gaskets, encapsulants for electronic devices, and numerous other medical/dental applications.

In another aspect of the present invention, an optically clear, thermoset polyurethane urea elastomer and a process for its preparation are provided. The optically clear, thermoset polyurethane urea elastomer of the present invention has the following general formula:

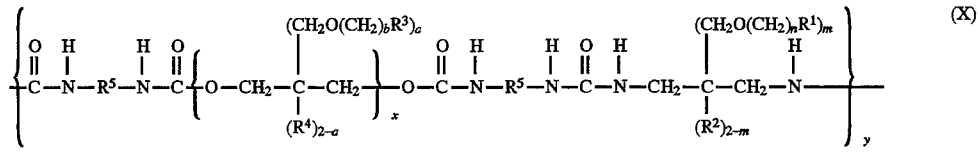

(X)

In Formula X, $R^1$ and $R^3$ are independently selected and are functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ and $R^4$ are independently selected and are functional groups including, but not limited to, lower alkyls having from 1 to 4 carbon atoms. $R^5$ is a functional group including, but not limited to, alkyl and aryl radicals. In Formula X, the indexes "m" and "a" are independently selected and represent integers having a value of 1 or 2; the indexes "n" and "b" are independently selected and represent integers having a value ranging from 1 to about 10; the index "x" represents an integer having a value ranging from 8 to about 150; and the index "y" represents an integer having a value ranging from 5 to about 250.

The optically clear, thermoset polyurethane urea elastomers of the present invention exhibit a wide variety of useful properties including, but not limited to, the following:

1) Elastomeric properties;
2) Optically clear, low refractive indices;
3) More hydrophobic and non-stick than Teflon;
4) Processable into thin coatings or bulk articles;
5) Flexible down to about −50° C.;
6) Bondable to a variety of substrates; and
7) Useful ambient temperature range from about −50° C. to about 240° C.

As such, the optically clear, thermoset polyurethane urea elastomers of the present invention have a variety of applications including, but not limited to, contact lens, intraocular lens, coatings for glasses, binoculars, windshields, and glass windows.

In yet another aspect of the present invention, a fluorinated polyamide is provided, the fluorinated polyamide having the general formula:

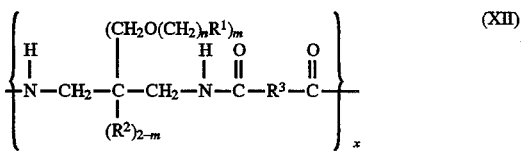

(XII)

In the above formula, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, lower alkyls having from 1 to 4 carbon atoms. $R^3$ is a functional group including, but not limited to, alkyl and aryl radicals. The index "m" represents an integer having a value of 1 or 2; the index "n" represents an integer having a value ranging from 1 to about 10; and the index "x" represents an integer having a value ranging from 5 to about 250.

In still a further aspect of the present invention, a fluorinated polyimide is provided, the fluorinated polyimide having the general formula:

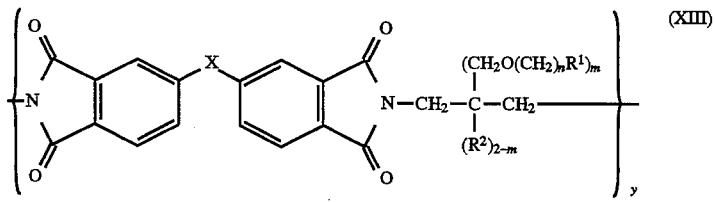

(XIII)

In Formula XIII, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, lower alkyls having from 1 to 4 carbon atoms. X is a functional group including, but not limited to, the following: a valence bond, —O—, >$SO_2$, >$CH_2$, >$C(CH_3)_2$ and >$C(CF_3)_2$. The index "m" represents an integer having a value of 1 or 2; the index "n" represents an integer having a value ranging from 1 to about 10; and the index "y" is an integer having a value ranging from 5 to about 400.

In addition to the fluorinated polyimide of Formula XIII, the present invention also provides a fluorinated polyimide having the general formula:

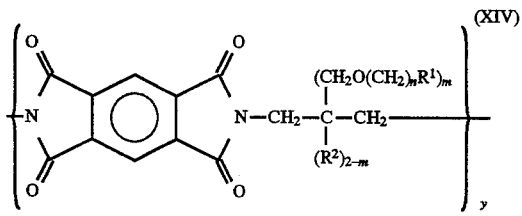

(XIV)

In Formula XIV, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, lower alkyls having from 1 to 4 carbon atoms. The index "m" represents an integer having a value of 1 or 2; the index "n" represents an integer having a value ranging from 1 to about 10; and the index "y" is an integer having a value ranging from 5 to about 400.

The polyimides prepared using the fluorinated diamines of the present invention have higher thermal stabilities and lower dielectric constants than polyimides prepared with traditional diamines. These properties result, in part, from the fact that in the fluorinated diamines of the present invention, the end groups are primary amino groups which are substantially removed from the perfluoroalkyl groups. Moreover, the fluorine is present in the side chains which allows the fluorocarbon segments to migrate to the polymer/air interface, thereby providing polymer surfaces with high fluorine concentrations. As such, the polyimides of the present invention can advantageously be used as polymeric insulators in the preparation of printed circuit boards and other electronic devices as well as in other applications, such as coatings for use in adverse environments such as space, etc.

In a further aspect of the present invention, the fluorinated diamines of the present invention can be used as curing agents to form fluorinated, cross-linked epoxy polymers. As such, the present invention provides a fluorinated, cross-linked epoxy polymer and a process for its preparation. More particularly, the present invention provides a process for the preparation of a fluorinated, cross-linked epoxy polymer, the process comprising: (a) mixing a glycidyl ether resin with a fluorinated diamine of the present invention to form a mixture; (b) casting the mixture into a mold; (c) de-gassing the cast mixture; and (d) curing the cast mixture at a temperature of between about 0° C. and 120° C. The fluoridated epoxy polymers prepared using the fluorinated diamines of the present invention have improved properties over traditional epoxy polymers and, thus, are useful as potting compounds for electronic equipment or other equipment that needs protection from moisture, coatings for submarine antennas, seals for chemical storage tanks, underwater hull coatings, and a variety of dental and medical applications (e.g., artificial joints).

Other advantages, objects, features and embodiments of the present invention will become apparent from the detailed description which follows.

DETAILED DESCRIPTION OF THE INVENTION AND PREFERRED EMBODIMENTS

In one aspect of the present invention, a fluorinated diamine is provided, the fluorinated diamine having the general formula:

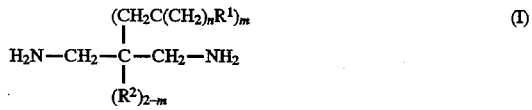

(I)

In Formula I, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. As used herein, the term "fluoroalkyl" refers to an alkyl radical wherein some or all of the hydrogen atoms have been replaced by fluorine. The alkyl group may be perfluorinated or, alternatively, it may include cites along the alkyl chain wherein the hydrogen atoms have not be replaced (e.g., omega-hydroperfluoroalkyl). $R^2$ is a functional group including, but not limited to, lower alkyls having from 1 to 4 carbon atoms. X is a functional group including, but not limited to, a valence bond —NR—, —O—, —S—, —$SO_2$—, and —N(R)SO$_2$—. The index "m" represents an integer having a value of 1 or 2. The index "n" represents an integer having a value ranging from 1 to about 10.

In a presently preferred embodiment, the fluorinated diamines of the present invention have the general formula:

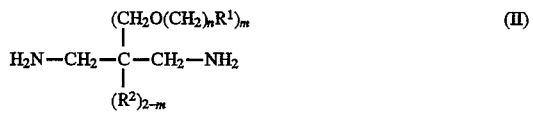

In Formula II, R$^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. As used herein, the term "fluoroalkyl" refers to an alkyl radical wherein some or all of the hydrogen atoms have been replaced by fluorine. The alkyl group may be perfluorinated or, alternatively, it may include cites along the alkyl chain wherein the hydrogen atoms have not be replaced (e.g., omega-hydroperfluoroalkyl). R$^2$ is a functional group including, but not limited to, lower alkyls having from 1 to 4 carbon atoms. The index "m" represents an integer having a value of 1 or 2. The index "n" represents an integer having a value ranging from 1 to about 10.

Within the scope of Formula II, certain fluorinated diamines are preferred, namely those in which R$^1$ is a perfluoroalkyl including, but not limited to, the following: trifluoromethyl, pentafluoroethyl, heptafluoropropyl, tridecafluorohexyl, pentadecafluoroheptyl, heptadecafluorooctyl, nonafluorobutyl, heneicosafluorodecyl and mixtures thereof. Further preferred are the fluorinated diamines in which R$^2$ is a lower alkyl including, but not limited to, methyl and ethyl. Examples of preferred fluorinated diamines include those in which: R$^1$ is trifluoromethyl, R$^2$ is methyl or ethyl, n is 1 and m is 1; R$^1$ is trifluoromethyl, n is 1 and m is 2; R$^1$ is pentafluoroethyl, R$^2$ is methyl or ethyl, n is 1 and m is 1; R$^1$ is pentafluoroethyl, n is 1 and m is 2; R$^1$ is heptafluoropropyl, R$^2$ is methyl or ethyl, n is 1 and m is 1; R$^1$ is heptafluoropropyl, n is 1 and m is 2; R$^1$ is tridecafluorohexyl, R$^2$ is methyl or ethyl, n is 2 and m is 1; R$^1$ is tridecafluorohexyl, n is 2 and m is 2; R$^1$ is tridecafluorohexyl, R$^2$ is methyl, n is 2, and m is 1; R$^1$ is pentadecafluoroheptyl, R$^2$ is methyl, n is 2, and m is 1; R$^1$ is pentadecafluoroheptyl, n is 2, and m is 2; R$^1$ is heptadecafluorooctyl, R$^2$ is methyl or ethyl, n is 1, and m is 1; R$^1$ is heptadecafluorooctyl, n is 1, and m is 2; R$^1$ is heneicosafluorodecyl, R$^2$ is methyl or ethyl, n is 2 and m is 1; R$^1$ is heneicosafluorodecyl, n is 2 and m is 2; R$^1$ is a mixture of trifluorohexyl, heptadecafluorooctyl and heneicosafluorodecyl, R$^2$ is methyl, n is 2, and m is 1; and R$^1$ is a mixture of trifluorohexyl, heptadecafluorooctyl and heneicosafluorodecyl, n is 2, and m is 2. Examples of fluorinated diamines of the present invention are set forth in Table I, infra.

TABLE I

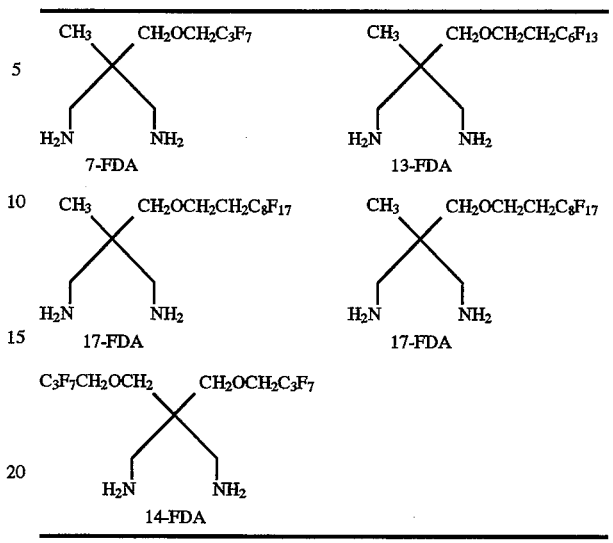

The fluorinated diamines of Formulae I and II can be prepared using a number of different synthetic schemes which employ, as starting materials, fluorinated oxetanes having the formula:

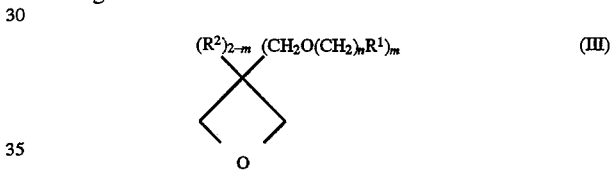

In Formula III, R$^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. R$^2$ is a functional group including, but not limited to, lower alkyls having from 1 to 4 carbon atoms. The index "m" represents an integer having a value of 1 or 2. The index "n" represents an integer having a value ranging from 1 to about 10. Such fluorinated oxetane compounds and their methods of preparation are described in copending, commonly assigned U.S. patent application Ser. No. 08/371,914, filed Jan. 12, 1995, (pending) the teachings of which are hereby incorporated by reference for any and all purposes. Examples of oxetanes which can be used to form the fluorinated diamines of the present invention are set forth in Table II, infra.

TABLE II

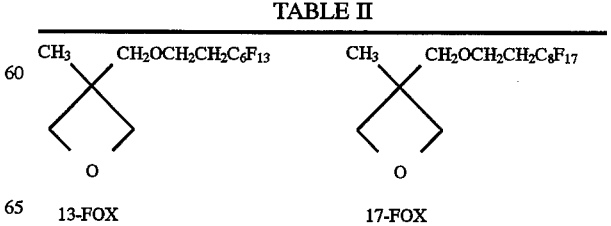

TABLE II-continued

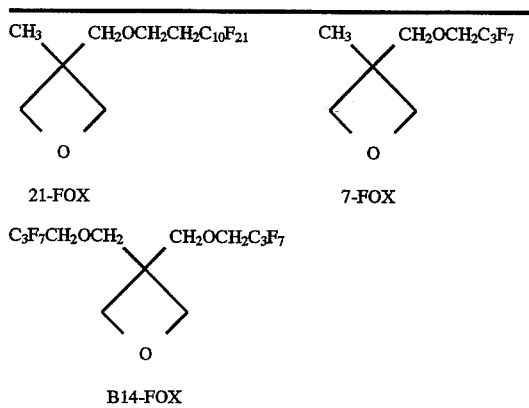

Briefly, the fluorinated oxetane monomers suitable for use in forming the fluorinated diamines of the present invention can be obtained by the reaction of aryl sulfonate derivatives of hydroxyalkyl oxetanes with fluorinated alkoxides in the presence of a polar aprotic solvent. The aryl sulfonate derivatives of the hydroxyalkyl oxetanes have the general formula:

In Formula IV, R is a functional group including, but not limited to, monocyclic aryl radicals having from six to ten carbon atoms (i.e., $C_6$ to $C_{10}$ monocyclic aryl radical) and acyclic, alkyl radicals having from one to four carbon atoms. Such monocyclic aryls include, but are not limited to, the following: benzyl, tolyl, xylyl and mesityl. Such acyclic, alkyls include, but are not limited to, the following: methyl, ethyl and trifluoromethyl. $R^1$ is a functional group including, but not limited to, the following: hydrogen and lower alkyls, having from 1 to 4 carbon atoms. The index "m" represents an integer having a value of 1 or 2. Certain sulfonates are preferred, namely the toluene sulfonates, such as the p-toluene sulfonate derivatives of 3-hydroxymethyl-3-methyloxetane and 3,3-bis(hydroxymethyl)oxetane.

The fluorinated alkoxides are obtained by the reaction of a fluorinated alcohol with sodium hydride in a suitable solvent such as, for example, dimethylformamide (i.e., DMF). Although sodium hydride is the preferred base for this reaction, other bases such as potassium hydride, potassium t-butoxide, calcium hydride, sodium hydroxide, potassium hydroxide, $NaNH_2$, n-butyl lithium and lithium diisopropylamide can also be used. Moreover, although the preferred solvent is DMF, other solvents such as dimethylacetamide (DMAC), dimethyl sulfoxide (DMSO), hexamethylene phosphoramide (HMPA), tetrahydrofuran (THF) and glyme can be used.

The fluorinated alcohols which can be used to make the fluorinated alkoxides have the general formula:

$$R^1(CH_2)_nOH \qquad (V)$$

In Formula V, $R^1$ is a functional group including, but not limited to, the following: linear or branched chain perfluoroalkyls, having from 1 to 20 carbon atoms; omega-hydroperfluoroalkyls, having from 1 to 20 carbon atoms; and oxa-perfluorinated polyethers, having from 4 to about 60 carbon atoms. The index "n" represents an integer having a value ranging from 1 to about 10. Examples of suitable fluorinated alcohols include, but are not limited to, the following: trifluoroethanol, heptafluorobutanol, pentadecafluorooctanol, tridecafluorooctanol, and the like. Other alcohols which are useful in forming the fluorinated alkoxides include fluorinated alcohols having the following formulae:

$$HOCH_2CF_2(OCF_2CF_2)_x-F \qquad (VI)$$

and $$HOCH_2CH_2NRSO_2(CF_2)_x-F \qquad (VIII)$$

In Formulae VI, VII and VIII, R is a functional group including, but not limited to, hydrogen and lower alkyls having from 1 to 4 carbon atoms; and the index "x" represents an integer having a value ranging from 1 to about 20. The above displacement reaction can be conducted at temperatures ranging from about 25° C. to about 150° C., however, the preferred temperature is between about 75° C. and about 85° C.

In addition to the foregoing method, another method has been developed for preparing fluorinated oxetanes in high-yields. This process eliminates the use of organic solvents and strong bases, such as NaH, which, in turn, reduces hazardous waste generation and air emissions of volatile organic compounds. In this process, a mixture of 3-haloalkyl-3-methyloxetane or 3,3-bis(haloalkyl)oxetane, a fluoroalcohol, a base (e.g., sodium hydroxide or potassium hydroxide) and a phase transfer catalyst is heated in an aqueous medium at a temperature of about 80° C. to about 85° C. until GLC analysis reveals complete consumption of the starting materials. Upon completion of the reaction, the product is recovered by separation and distillation of the organic phase. The organic phase contains most of the fluorinated oxetane. The recovered fluorinated oxetane is polymer grade and has a purity normally in excess of 99%. Isolated yields are high and range from 80% to 90% for the purified fluorinated oxetane. Yields prior to separation and purification exceed 90% for the crude product.

In this process, the phase transfer catalysts functions by transferring the counterion so that it is more soluble in the organic phase. A variety of phase transfer catalysts can be used in this process. Suitable phase transfer catalysts include, but are not limited to, the following: tetramethylammonium bromide, tetraethylammonium bromide, tetramethylammonium iodide, ethyltributylammonium bromide, crown ethers, glycols, etc. In a presently preferred embodiment, the preferred phase transfer catalyst is tetrabutylammonium bromide due to its relatively low cost and good solubility in both organic and aqueous mediums. In addition, a variety of bases can be used in this process. Examples of suitable bases include, but are not limited to, calcium hydroxide, magnesium hydroxide, tetrabutylammonium hydroxide, etc. In a presently preferred embodiment, sodium hydroxide or potassium hydroxide are used as the base because they are readily available in large quantities and are relatively inexpensive.

The above reaction can be conducted at temperatures as low as 25° C. and as high as 120° C. and, more preferably, at temperatures ranging from about 80° C. to about 100° C. However, at low temperatures, the rate of displacement is extremely slow and competing side reactions such as hydrolysis start to dominate. At higher temperatures, the rate of displacement is extremely fast, requiring specialized equipment that can handle pressure, thus making the process uneconomical and unattractive for commercial scale-up.

Once formed, the fluorinated oxetanes of Formula III can be subsequently reacted to produce the fluorinated diamines of the present invention (see, Formulae I and II, supra). More particularly, fluorinated oxetanes, substituted at the 3-position with either one or two fluorinated alkyl groups, can be converted to the corresponding 1,3-diaminopropane derivatives using the 4-step process illustrated in Scheme 1, infra.

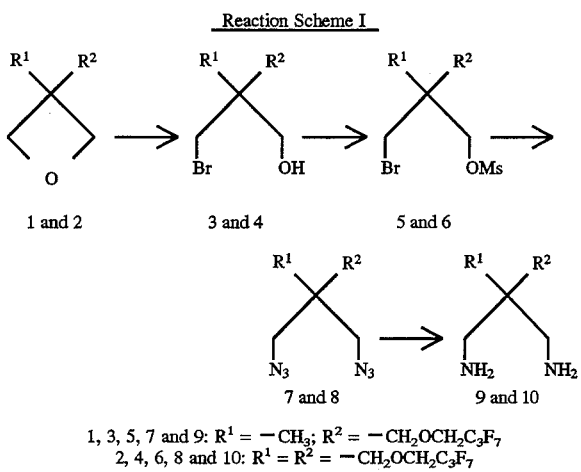

1, 3, 5, 7 and 9: $R^1 = -CH_3$; $R^2 = -CH_2OCH_2C_3F_7$
2, 4, 6, 8 and 10: $R^1 = R^2 = -CH_2OCH_2C_3F_7$ In the first step, fluorinated oxetanes, e.g., 3-heptafluorobutoxymethyl-3-methyloxetane (1) and 3,3-bis (heptafluorobutoxymethyl)oxetane (2), were reacted with 48% HBr to give ring-opened products, 3-bromo-2-heptafluorobutoxymethyl-2-methyl-1-propanol (3) and 3-bromo-2,2-bis(heptafluorobutoxymethyl-1-propanol (4), in 94% and 89% yields, respectively. This reaction is conducted in an aqueous medium, and the product is isolated by a simple purification process. No further purification is needed, and the crude product is used directly in the subsequent mesylation reaction.

In the second step, hydroxy compounds 3 and 4 are reacted with methanesulfonyl chloride to give the corresponding mesylates 5 and 6 in 95–96% yield. It will be readily apparent to those of skill in the art that other leaving groups, such as tosylate and triflate, can be used in place of mesylate. The mesylation reaction is conducted in methylene chloride at a temperature of about 5° C. to about 10° C. in the presence of an organic base, e.g., triethylamine. It will be readily apparent to those of skill in the art that solvents such as chloroform, toluene, hexane, and carbon tetrachloride, and organic bases such as pyridine and dimethylaminopyridine(DMAP), can also be used to achieve the above conversion. Compounds 5 and 6 are oils and can be stored at room temperature for several months.

Reaction of compounds 5 and 6 with sodium azide in dimethylformamide (DMF) at 115° C. gives the corresponding diazides, 1,3-diazido-2-heptafluorobutoxymethyl-2-methylpropane (7) and 1,3-diazido-2,2-bis (heptafluorobutoxymethyl)propane (8), in 91% and 97% yields, respectively. The reaction requires about 48 hrs to reach completion as indicated by GLC analysis. The slow rate of the displacement reaction is attributed to the steric hindrance encountered in displacing a mesylate or bromo group from a neopentyl carbon. It will be readily apparent to those of skill in the art that other solvents, such as dimethyl sulfoxide (DMSO), acetone, diethylene glycol, diglyme, hexamethylphosphoramide (HMPA), etc., can be used for the displacement reaction, but do not offer any major advantages. The diazides 7 and 8 are oils at room temperature and are used without purification in the subsequent reduction.

In the final step, diazides 7 and 8 are reduced to diamines, 1,3-diamino-2-heptafluorobutoxymethyl-2-methylpropane (9) and 1,3-diamino-2,2-bis(heptafluorobutoxymethyl) propane (10), by hydrazine-mediated catalytic-transfer hydrogenation (see, Malik, et al., Synthesis, 450 (1989)). The yields of diamines 9 and 10 by this process are 85% and 72%, respectively. Catalytic transfer hydrogenation is a convenient bench scale process for reducing diazides, since it can be conducted in normal glassware at atmospheric pressure. On a larger scale, conventional hydrogenation can be used to produce fluorinated diamines. The progress of the reaction is monitored by GLC and by following the disappearance of the azide stretching band at 2100 $cm^{-1}$ in the infrared spectrum. Diamines 9 and 10 are colorless liquids and can be purified by distillation to give materials that are >99% pure by GLC analysis. The diamines are characterized by GLC, $^1H$ and $^{13}C$ NMR, IR, and combustion analysis.

In a manner similar to that previously described, diamines having longer fluorinated side chains can be prepared (see, Reaction Scheme II). Briefly, in the first step, a mixture of fluorinated oxetanes 11 (e.g., 3,3,4,4,5,5,6,6,7,7,8,8,8-tridecafluorooctyloxymethyl-, 3,3,4,4,5,5,6,6,7,7,8,8,-9,9,10,10,10-heptadecafluorodecyloxymethyl-, and 3,3,4,4,5,5,6,6,7,7,8,8,9,9,10,10,-11,11,12,12,12-heneicosafluorododecyloxymethyl-3-methyloxetane) is reacted with 48% HBr to give the ring-opened products. In the second step, the hydroxy compounds 12 are reacted with, for example, methanesulfonyl chloride to give the corresponding mesylates 13. In the third step, the mesylates 13 are reacted with sodium azide in dimethylformamide (DMF) at about 115° C. to give the corresponding diazides 14. Thereafter, the diazides 14 are reduced to the corresponding diamines 15 by hydrazine-mediated catalytic-transfer hydrogenation. Using this procedure, other fluorinated diamines with longer fluorinated side chains can be readily prepared.

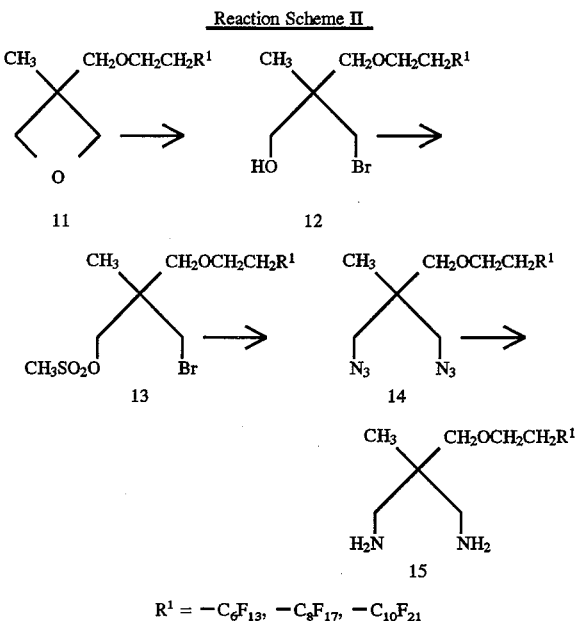

$R^1 = -C_6F_{13}, -C_8F_{17}, -C_{10}F_{21}$

As such, using the method described above, the fluorinated diamines of the present invention can readily be prepared. The fluorinated diamines of the present invention are highly nucleophilic and are structured to provide polymeric materials having optimal surface properties. As illustrated in Formulae I and II, supra, the end groups of the fluorinated diamines are primary amino groups which are substantially removed from the perfluoroalkyl groups. Moreover, the fluorine is present in the side chains which allows the fluorocarbon segments to migrate to the polymer/air interface, thereby providing polymer surfaces with high fluorine concentrations. In addition, the fluorinated diamines of the present invention are miscible with highly fluorinated materials. This is a major advantage since the commercially available diamines are generally not miscible with fluorinated monomers. The high miscibility of the fluorinated diamines of the present invention with fluorinated monomers makes it possible to prepare highly fluorinated polymers. Thus, the fluorinated diamines of the present invention can be used to form a variety of different polymers having useful properties. Polymers which can be formed using the fluorinated diamines of the present invention include, but not limited to, polyureas, polyurethane urea elastomers, polyamides, polyimides, epoxies etc.

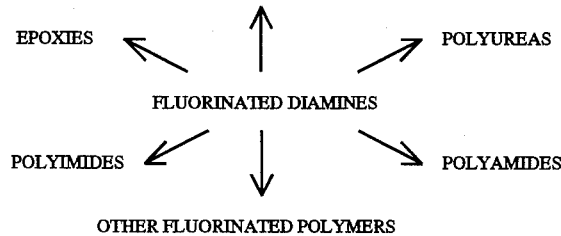

FLUORINATED POLYURETHANE UREA ELASTOMERS

EPOXIES   POLYUREAS

FLUORINATED DIAMINES

POLYIMIDES   POLYAMIDES

OTHER FLUORINATED POLYMERS

Generally, incorporation of fluorine into a polymer alters the properties of the resulting polymer in the following ways:

1. Thermal stability increases. Incorporation of fluorine into the polymer extends the upper use temperature of the polymer and allows the polymer to be processed at higher temperatures without degradation. Increased thermal stability allows the fluoropolymers to be used in environments where other hydrocarbon-based polymers cannot be used.

2. Surface energy decreases. Incorporation of fluorine into the polymer improves the release characteristics of the polymer, i.e., it makes the polymer non-stick. Polymers with improved release characteristics, i.e., improved non-stick properties, can be used as backing for adhesive tapes, release coatings for molds, ice-release coating, fouling release coatings for ship hulls, etc.

3. Refractive index decreases. Optically clear polymers with low refractive indices are useful for a variety of optical applications such as contact lenses, intraocular lenses, coatings for optical instruments, claddings for optical fibers, etc.

4. Coefficient of friction decreases. Incorporation of fluorine into the polymer reduces friction and, thus, improves lubricity. Coatings that reduce friction can be used for a variety of applications such as coatings for vehicle seals, windshield wipers, drag reducing coatings for sail boats, coatings for magnetic disk drives, etc.

5. Hydrophobicity increases. Incorporation of fluorine into the polymer improves the water repellency and moisture barrier characteristics of the polymer. Polymers with improved moisture resistant properties are useful as potting compounds for electronic devices, moisture barrier films and coatings, rain erosion coatings, anti-corrosion coatings, etc. Such polymers can be used in applications where exclusion of moisture is critical.

6. Oleophobicity increases. Incorporation of fluorine into the polymer increases the oil repellency of the polymer, thereby making the polymer useful as a stain resistant coating for garments, carpets, etc.

7. Flammability decreases. Incorporation of fluorine into the polymer improves the flame retardancy of the polymer. Thus, such polymers can be used, for example, as flame retardant coatings in the garment industry.

8. Environmental stability increases. Incorporation of fluorine into the polymer improves the environmental stability of the polymer, thereby making the polymer more stable when exposed, for example, to ultraviolet (UV) light and moisture. The increased environmental stability makes fluoropolymers an excellent choice for outdoor applications.

As such, polymers formed from the fluorinated diamines of the present invention have useful properties including, but not limited to, increased thermal stability, decreased surface energy, decreased refractive index, decreased coefficient of friction, increased hydrophobicity, increased oleophobicity, decreased flammability and increased environmental stability. Thus, polymers formed from the fluorinated diamines of the present invention have commercial applications as fouling and ice release coatings, drag reduction coatings, moisture barrier coatings; encapsulants for electrical devices; curing agents for epoxies; catheters; artificial prosthesis components such as joints, hearts and valves; contact lenses; intraocular lenses; films, paints; adhesives; non-transfer cosmetics; water repellent coatings; oil/stain resistant coatings; incendiary binders; lubricants, and the like.

Thus, in another aspect of the present invention, a fluorinated polyurea is provided, the fluorinated polyurea having the following general formula:

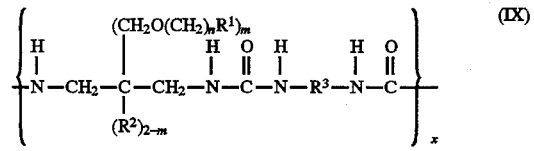

In Formula IX, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. As used herein, the term "fluoroalkyl" refers to an alkyl radical wherein some or all of the hydrogen atoms have been replaced by fluorine. The alkyl group may be perfluorinated or, alternatively, it may include cites along the alkyl chain wherein the hydrogen atoms have not be replaced (e.g., omega-hydroperfluoroalkyl). $R^2$ is a functional group including, but not limited to, lower alkyls having from 1 to 4 carbon atoms. $R^3$ is a functional group including, but not limited to, alkyl and aryl radicals. The index "m" represents an integer having a value of 1 or 2; the index "n" represents an integer having a value ranging from 1 to about 10; and the index "x" is an integer having a value ranging from 5 to about 250.

Within the scope of Formula IX, certain fluorinated polyureas are preferred, namely those in which $R^1$ is a perfluoroalkyl including, but not limited to, the following: trifluoromethyl, pentafluoroethyl, heptafluoropropyl, tridecafluorohexyl, pentadecafluoroheptyl, heptadecafluorooctyl and heneicosafluorodecyl. Also preferred are the fluorinated polyureas in which $R^2$ is a lower alkyl including, but not limited to, methyl and ethyl. Equally preferred are the fluorinated polyureas in which $R_3$ is an alkyl or aryl radical including, but not limited to, the following:

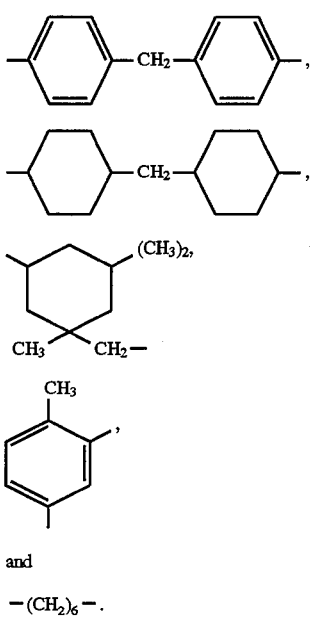

and $-(CH_2)_6-$.

Using the polymerization method set forth in the Example Section, the fluorinated diamines of Formulae I and II can be reacted with a variety of di- and polyisocyanates to form the fluorinated polyureas of Formula IX. The polymerization reaction can be carried out at a temperature ranging from about 10° C. to about 200° C. and, more preferably, at about room temperature. In general, any di- or polyisocyanate can be used in the polymerization reaction. Suitable di- and polyisocyanates include, but are not limited to, the following: 1,6-diisocyanatohexane (HDI), tolylene 2,4-diisocyanate (TDI), methylene bis-(4-phenylisocyanate) (MDI), hydrogenated methylene bis-(4-phenylisocyanate) (Des-W), isophorone diisocyanate (IPDI), polymeric 1,6-diisocyanatohexane (N- 100 and N-3200), cyclohexylene-1,4-diisocyanate and 2,2,4-trimethylhexamethylene diisocyanate. In a presently preferred embodiment, HMDI and IPDI are used. The polymerization reaction can be carried out with or without the use of a solvent. In a presently preferred embodiment, no solvent is used. If, however, a solvent is used, suitable solvents include, but are not limited to, dimethylformamide (DMF), dimethylacetamide (DMAC), THF and mixtures thereof. Generally, the isocyanate:fluorinated diamine ratio is about 0.8 to 1.3 and, more preferably, about 0.9 to 1.1. The fluorinated diamines of the present invention react exothermically with di- or polyisocyanates, even in the absence of a catalyst, to form high molecular weight fluorinated polyureas. The high reactivity of the fluorinated diamines makes them ideal candidates for commercial processes such as reaction injection molding (RIM). For coating applications, the rate of polymerization can be retarded by adding a small amount of solvent such as THF.

For example, 1,3-diamino-2-heptafluorobutoxymethyl-2-methylpropane (9) and 1,3-diamino-2,2-bis(heptafluorobutoxymethyl)propane (10), prepared using the method set forth in Reaction Scheme I, were reacted with HDI and IPDI to form polyureas of Formulae I and II. The fluorinated polyureas prepared from diamines 9 or 10 and HMDI were soluble in DMF and sulfuric acid, but were insoluble in other solvents such as toluene, Freon, chloroform, and methanol. In contrast, the polyurea from 9 and IPDI is soluble in DMF, THF, acetone and sulfuric acid. If desired, thin films of polyureas could be cast from the solution of these materials in DMF. Thermal analysis (DSC and TGA) reveal that these fluorinated polyureas undergo major degradation in air at approximately 320° C.

The fluorinated polyureas of Formula IX exhibit a wide variety of useful properties including, but not limited to, the following: hydrophobic properties, low surface energies, low dielectric constants, high abrasion resistance and tear strength, low coefficients of friction, high adhesion and low refractive indices. Combinations of these properties make the fluorinated polyureas of the present invention extremely attractive for a variety of applications including, but not limited to, anti-fouling (release) coatings, ice release coatings, corrosion resistant coatings, automotive top coats (e.g., car wax), oil/soil resistant coatings, seals and gaskets, encapsulants for electronic devices, and numerous other medical/dental applications.

In addition to the foregoing polymers, polymers with low refractive indices are needed for use as claddings for optical fibers. A high premium is paid for materials with low refractive indices. The material currently being used as cladding for optical fibers is Teflon AF, an optically clear fluoropolymer. Unfortunately, this material is expensive and somewhat difficult to process. Moreover, this material is prone to crack or scratch when dropped or handled roughly. Defects such as cracks and scratches increase light scattering and, thus, reduce the efficiency of the optical fibers. As such, a need exists for a fluorinated polymer that is elastomeric, optically clear with a low refractive index, tough and relatively inexpensive and simple to process.

As such, in another aspect of the present invention, an optically clear, thermoset polyurethane urea elastomer and a process for its preparation are provided. The optically clear, thermoset polyurethane urea elastomer of the present invention has the following general formula:

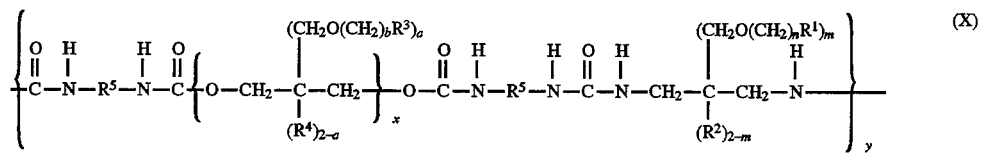

In Formula X, $R^1$ and $R^3$ are independently selected and are functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ and $R^4$ are independently selected and are functional groups including, but not limited to, lower alkyls having from 1 to 4 carbon atoms. $R^5$ is a functional group including, but not limited to, alkyl and aryl radicals. In Formula X, the indexes "m" and "a" are independently selected and represent integers having a value of 1 or 2; the indexes "n" and "b" are independently selected and represent integers having a value ranging from 1 to about 10; the index "x" represents an integer having a value ranging from 8 to about 150; and the index "y" represents an integer having a value ranging from 5 to about 250.

Within the scope of Formula X, certain fluorinated polyurethane urea elastomers are preferred, namely those in which $R^1$ is a perfluoroalkyl including, but not limited to, the following: trifluoromethyl, pentafluoroethyl, heptafluoropropyl, tridecafluorohexyl, pentadecafluoroheptyl, heptadecafluorooctyl and heneicosafluorodecyl. Also preferred are the fluorinated polyurethane urea elastomers in which $R^2$ is a lower alkyl including, but not limited to, methyl and ethyl. Equally preferred are the fluorinated polyurethane urea elastomers in which $R^5$ is an alkyl or aryl radicals including, but not limited to, the following:

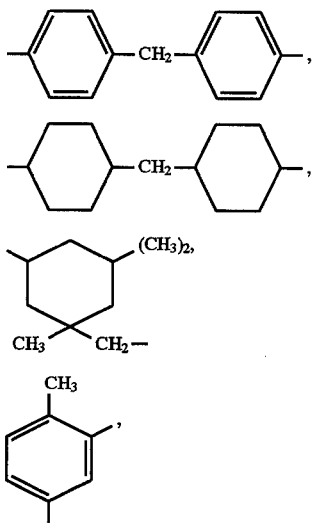

and

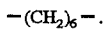

In addition, a process for the preparation of an optically clear, thermoset polyurethane urea elastomer is provided, the process comprising: (a) providing a fluorinated prepolymer; (b) premixing the fluorinated prepolymer with a diisocyanate, a catalyst and a solvent at a temperature between about 25° C. and about 100° C. to form a first mixture; (c) providing a fluorinated diamine; (d) mixing the fluorinated diamine with the first mixture to form a second mixture; (e) casting the second mixture into a mold; (f) de-gassing the cast mixture; and (g) curing the cast mixture at a temperature of between about 20° C. and 150° C.

The fluorinated diamine used in the above method has the general formula

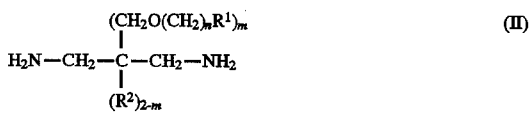

As previously described, in Formula II, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, lower alkyls having from 1 to 4 carbon atoms. The index "m" represents an integer having a value of 1 or 2. The index "n" represents an integer having a value ranging from 1 to about 10.

The fluorinated prepolymer used to prepare the optically clear, thermoset polyurethane urea elastomer is a fluorinated polyol. Suitable fluorinated polyols include, but are not limited to, alcohol-terminated fluorinated polyethers which are commercially available from Ausimono U.S.A., Inc. (Morristown, N.J.) and 3M (St. Paul, Minn.), and the fluorinated polyols described in copending, commonly assigned U.S. Pat. application Ser. No. 08/371,914, filed Jan. 12, 1995 (pending), the teachings of which are hereby incorporated by reference for any and all purposes.

In a presently preferred embodiment, the fluorinated prepolymer has the general formula:

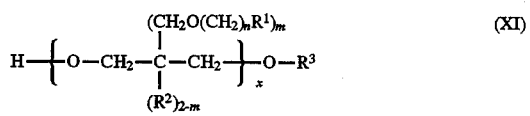

In Formula XI, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, the following: hydrogen and alkyls, having from 1 to 4 carbon atoms. $R^3$ is a functional group including, but not limited to, the following: hydrogen and hydroxy alcohols having from 2 to 5 carbons and 1 to 3 hydroxy groups. The index "n" represents an integer having a value ranging from 1 to about 10; the index "m" represents an integer having a value of 1 or 2; and the index "x" represents an integer having a value ranging from 5 to about 250.

The fluorinated prepolymer of Formula XI can be prepared by polymerizing the fluorinated alkoxy oxetanes of Formula III, supra, using conventional procedures. More particularly, the fluorinated prepolymer are formed from the oxetane monomers by cationic polymerization. This technique employs an initiator and a Lewis acid for cationic polymerization. Suitable Lewis acids, i.e., compounds capable of accepting a pair of electrons, include, but are not limited to, the following: boron trifluoride etherate, boron trifluoride, fluoroboric acid, or aluminum, phosphorous and antimony halides. Suitable initiators are polyhydroxy aliphatic compounds such as alkyl and isoalkyl polyols, having from 2 to about 5 carbon atoms and from 2 to 4 hydroxyl groups. Such initiators include, but are not limited to, the following: ethylene glycol, butane-1,4-diol, propylene glycol, isobutane-1,3-diol, pentane-1,5-diol, and pentaerythritol.

The polymerization is conducted in the presence of a suitable inert solvent, preferably a halogenated $C_1$ to $C_5$ hydrocarbon. Examples of such halogenated hydrocarbons include, but are not limited to, the following: methylene chloride, methylene bromide, ethylene dichloride, ethylene dibromide, propylene dichloride, Freons* and fluorinated solvents. The catalyst and initiator are preferably mixed in the solvent prior to the addition of the oxetane monomer. An example of a preferred catalyst, initiator and solvent combination is boron trifluoride tetrahydrofuranate ($BF_3 \cdot THF$) and butane-1,4-diol in methylene chloride.

To this mixture, the oxetane monomer is added and solution polymerization is practiced at solution concentrations from about 5 to about 75 weight percent. The length of the polymer chain is largely dependent upon the molar equivalents of the monomer (m) and the initiator (n), the average chain length being approximately m/n mer units long. As such, the concentration of the catalyst and the proportion of the initiator, e.g., butane-1,4-diol, can be varied to control the molecular weight of the polymer, with higher proportions of initiator resulting in the polymer chain having a lower molecular weight. Useful proportions of catalyst (e.g., boron trifluoride etherate) to initiator (e.g., butane-1,4-diol) can range from about 100:1 to about 1:1, with 3:1 to 1:1 being the presently preferred range.

Generally, for use in accordance with the present invention, polyether chains are prepared having molecular weights (weight average) of between about 2,000 and about 25,000. Typically, the fluorinated prepolymer and the isocyanate are present in a ratio ranging from 1 to 2 to 1 to 20 and, more preferably, in a ratio ranging from 1 to 3 to about 1 to 5. Distribution of mer units throughout the polymer chains and polydispersity of the chains depends on specific polymerization conditions. Polyethers in accordance with the present invention generally have polydispersities between about 1.0 and about 2.5.

Once prepared, the fluorinated prepolymer is mixed with an isocyanate, a catalyst and a solvent at a temperature of about 25° C. to about 120° C. to prepare a first mixture. In a presently preferred embodiment, the fluorinated prepolymer is mixed with the isocyanate, the catalyst and the solvent at a temperature of about 50° C. to about 60° C. Suitable isocyanates include, but are not limited to, the following: 1,6-diisocyanatohexane (HDI), tolylene 2,4-diisocyanate (TDI), methylene bis-(4-phenylisocyanate) (MDI), hydrogenated methylene bis-(4-phenylisocyanate) (Des-W), isophorone diisocyanate (IPDI), polymeric 1,6-diisocyanatohexane (N-100 and N-3200), cyclohexylene-1, 4-diisocyanate, 2,2,4-trimethylhexmethylene diisocyanate and mixtures thereof. Suitable catalysts include, but are not limited to, dibutyltin dilaurate, ferric acetylacetonate, triethylamine, tin octonate, chromium acetylacetonate, triphenylbismuth/nitrosalicylic acid, triethylenediamine, lead octonate and mixtures thereof. Suitable solvents include, but are not limited to, the following: THF, toluene, trifluorotoluene, pyridine, Freon, methylene chloride and chloroform. Thereafter, the first mixture is mixed with a fluorinated diamine, supra, to form a second mixture. Typically, the catalyst and the fluorinated diamine are present at a concentration ranging from about 0.1% to about 15% (wt/wt).

Bulk materials are prepared by casting the second mixture in a mold or cavity, degassing the mixture, and then curing it at about 65° C. for 16 to 36 h. A thin film is prepared by diluting the above formulation with THF, spreading the mixture over the substrate with, for example, a Doctor's blade, and then curing the coated substrate in an oven at about 65° C. Alternately, the substrate can be dip-coated or spray coated and cured in an oven at about 65° C. The cure temperature can be between about 20° C. and about 150° C. The preferred temperature is about 65° C. The above formulation can be cured at room temperature by increasing the amount of catalyst to about 0.5%. The cure is also dependent on the thickness of the sample and the cross-linking agent, i.e., fluorinated diamine, used. Thin samples cure within 3 h at about 65° C., whereas a ⅛ inch thick sample takes between 8–16 h to cure.

The optically clear, thermoset polyurethane urea elastomers of the present invention exhibit a wide variety of useful properties including, but not limited to, the following:

1) Elastomeric properties;
2) Optically clear, low refractive indices;
3) More hydrophobic and non-stick than Teflon;
4) Processable into thin coatings or bulk articles;
5) Flexible down to about −50° C.;
6) Bondable to a variety of substrates; and
7) Useful ambient temperature range from about −50° C. to about 240° C.

As such, the optically clear, thermoset polyurethane urea elastomers of the present invention have a variety of applications including, but not limited to, contact lens, intraocular lens, coatings for glasses, binoculars, windshields, and glass windows.

In yet another aspect of the present invention, a fluorinated polyamide is prepared using the fluorinated diamines of Formulae I and II, the fluorinated polyamide having the general formula:

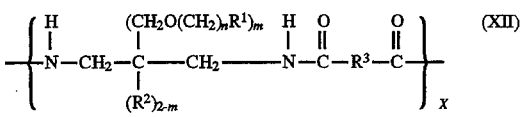

In the above formula, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, lower alkyls having from 1 to 4 carbon atoms. $R^3$ is a functional group including, but not limited to, alkyl and aryl radicals. The index "m" represents an integer having a value of 1 or 2; the index "n" represents an integer having a value ranging from 1 to about 10; and the index "x" represents an integer having a value ranging from 5 to about 250.

Within the scope of Formula XII, certain fluorinated polyamides are preferred, namely those in which $R^1$ is a perfluoroalkyl including, but not limited to, the following: trifluoromethyl, pentafluoroethyl, heptafluoropropyl, tridecafluorohexyl, pentadecafluoroheptyl, heptadecafluorooctyl and heneicosafluorodecyl. Also preferred are the fluorinated polyamides in which $R^2$ is a lower alkyl including, but not limited to, methyl and ethyl. Equally preferred are the fluorinated polyamides in which $R^3$ is an alkyl or aryl radical including, but not limited to, the following:

$-(CH_2)_p-$, $-(CF_2)_p-$,

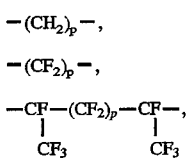

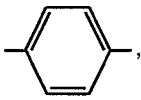

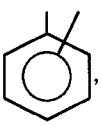

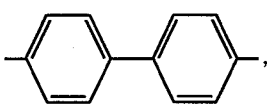

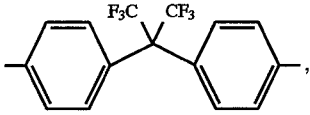

and

-continued

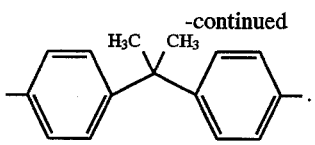

The polyamides of the present invention can be prepared by reacting a fluorinated diamine with a diacid chloride or a diacid. General procedures for the preparation of polyamides are disclosed in Yang, H. H., *Aromatic High Strength Fibers* (Wiley Interscience, N.Y., pp. 114–115 and 128–137 (1989)), the teachings of which are incorporated herein by reference. More particular, in one embodiment, a polyamide having the structure set forth in Formula XII is prepared by reacting a fluorinated diamine of the present invention with a diacid chloride in the presence of a base. This reaction can be carried out with or without the use of a solvent. In a preferred embodiment, no solvent is used. If, however, a solvent is used, suitable solvents include, but are not limited to, chloroform, methylene chloride, chlorobenzene, DMAC, DMF, toluene, THF and DMAC/LiCl. Suitable bases include, but are not limited to, triethylamine, pyridine and DABCO. Diacid chlorides which can be used to form the polyamides of the present invention have the general formula:

$$Cl-\overset{O}{\underset{\|}{C}}-R-\overset{O}{\underset{\|}{C}}-Cl$$

wherein R is an alkyl or aryl radical including, but not limited to, the following:

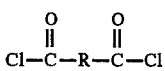

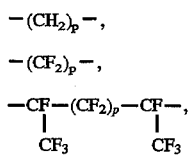

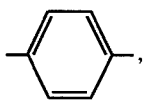

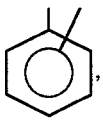

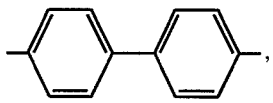

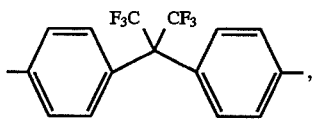

and

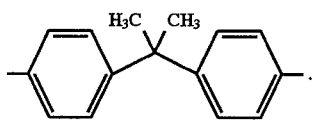

In an alternative embodiment, a polyamide having the structure set forth in Formula XII is prepared by reacting a fluorinated diamine of the present invention with a diacid (e.g., adipic acid) to form a salt. Subsequently, the salt is heated at a temperature of about 250° C. to about 300° C. to form a polyamide of Formula XII. Diacids which can be used to form the polyamides of the present invention have the general structure:

$$HO-\overset{O}{\underset{\|}{C}}-R-\overset{O}{\underset{\|}{C}}-OH$$

wherein R is an alkyl or aryl radical including, but not limited to, the following:

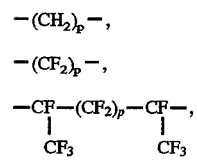

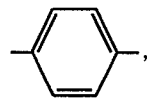

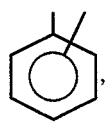

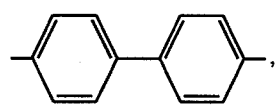

and

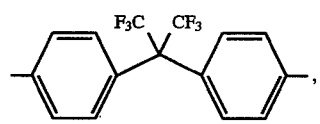

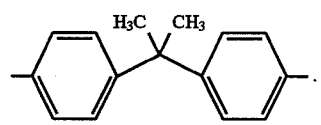

In another embodiment, it has been discovered that the fluorinated diamines of the present invention can be used to improve the properties of nylon, a synthetic polyamide. Nylon is prepared by reacting a diamine (e.g., 1,6-hexanediamine) with a diacid (e.g., adipic acid) or a diacid chloride. One of the problems with nylon is that it absorbs large amount of water, thereby limiting its use in high humidity environments, or in applications demanding high moisture resistance. Because the fluorinated diamines of the present invention have fluorine in the side chains, they are ideally structured for the preparation of polymers with low surface energies and high hydrophobicities. Polymers with fluorinated side chains provide optimum surface properties since fluorinated side chains phase separate and migrate to the polymer/air interface, providing a surface that is rich in fluorine. Thus, it has now been discovered that replacement of 2 to about 20% and, more preferably, of 5 to about 10% of the traditionally used diamines (e.g., 1,6-hexanediamine) with the fluorinated diamine of the present invention gives nylon having improved properties such as higher hydrophobicity, lower surface energy, improved oil/stain resistance and improved lubricity. In addition, nylon containing from 2 to about 20% of the fluorinated diamines of the present invention is easier to process because it eliminates the use of release agents in the molding process.

In still a further aspect of the present invention, a fluorinated polyimide is provided, the fluorinated polyimide having the general formula:

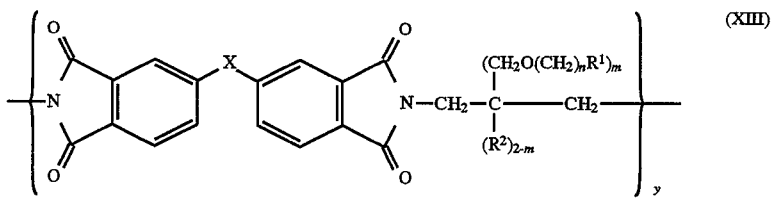

(XIII)

In Formula XIII, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, lower alkyls having from 1 to 4 carbon atoms. X is a functional group including, but not limited to, the following: a valence bond, —O—, >SO$_2$, >CH$_2$, >C(CH$_3$)$_2$ and >C(CF$_3$)$_2$. The index "m" represents an integer having a value of 1 or 2; the index "n" represents an integer having a value ranging from 1 to about 10; and the index "y" is an integer having a value ranging from 5 to about 400.

In addition to the fluorinated polyimide of Formula XIII, the present invention also provides a fluorinated polyimide having the general formula:

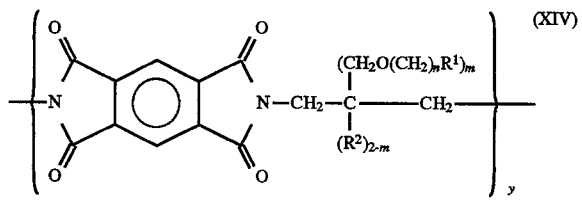

(XIV)

In Formula XIV, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, lower alkyls having from 1 to 4 carbon atoms. The index "m" represents an integer having a value of 1 or 2; the index "n" represents an integer having a value ranging from 1 to about 10; and the index "y" is an integer having a value ranging from 5 to about 400.

The fluorinated diamines of the present invention can be reacted with dianhydrides to form polyamic acid which, in turn, can be dehydrated to form polyimides of Formulae XIII and XIV. As such, the polyimides of the present invention are typically prepared using a two-step process. In the first step, a fluorinated diamine is condensed with a dianhydride in a polar, aprotic solvent to form a viscous solution of polyamic acid. This condensation reaction is carried out at a temperature ranging from 0° C. to about 100° C. and, more preferably, at about room temperature. Solvents suitable for use in this reaction include, but are not limited to, DMAC, DMF, toluene, xylene, chlorobenzene, ortho-dichlorobenzene and N-methylpyrolidone (NMP). Once formed, the polyamic acid solution is dehydrated in a second step to form a polyimide of Formulae XIII and XIV.

Dehydration of the polyamic acid can be achieved either thermally or chemically. In the thermal dehydration process, the polyamic acid is cast onto a substrate and the coated substrate is heated in an oven at about 100° C. to remove the solvent. Thereafter, the temperature is slowly ramped up to about 350° C. to effect cyclization and formation of the polyimide. In the chemical dehydration process, a solution of the polyamic acid is added to a solution of pyridine and acetic anhydride in NMP or DMAC at about 100° C. The mixture is typically heated at about 100° C. for 2 to 3 hours, and then isolated by precipitation into water. The product is washed with water to remove any residual solvent, and then heated to about 200° C. to remove any remaining water/solvent. (An example of this process is disclosed in U.S. Pat. No. 5,286,825 issued to Anton, et al., the teachings of which are incorporated herein by reference.)

Polyimides constitute an important class of polymers that are used mainly as a polymeric insulator in the preparation of printed circuit boards and other electronic packaging applications. To be useful as a polymeric insulator, the material must have high thermal stability and a low dielectric constant. With current emphasis on compact, lower weight electronic devices, major efforts have been devoted to developing materials that have high thermal stabilities and low dielectric constant. Materials with low dielectric constant are good insulators and allow closer packing of lines which, in turn, lead to smaller, more compact electronic equipment.

The polyimides prepared using the fluorinated diamines of the present invention have higher thermal stabilities and lower dielectric constants than polyimides prepared with traditional diamines. These properties result, in part, from the fact that in the fluorinated diamines of the present invention, the end groups are primary amino groups which are substantially removed from the perfluoroalkyl groups. Moreover, the fluorine is present in the side chains which allows the fluorocarbon segments to migrate to the polymer/air interface, thereby providing polymer surfaces with high fluorine concentrations. As such, the polyimides of the present invention can advantageously be used as polymeric insulators in the preparation of printed circuit boards and other electronic devices as well as in other applications, such as coatings for use in adverse environments such as space, etc.

In a further aspect of the present invention, the fluorinated diamines of Formulae I and II can be used as curing agents to form fluorinated, cross-linked epoxy polymers. Epoxy polymers generally consist of the following two part system: (1) a resin and (2) a curing agent (also known as a hardener). The resin is typically an aromatic glycidyl ether, and the curing agent or hardener is typically an aliphatic amine or an aromatic anhydride. Epoxy polymers are not known for their high resistance towards moisture and, thus, they are not used in high humidity environments or in environments in which the presence of moisture is problematic. In order to improve the water repellency characteristics of epoxy polymers, Griffith, et al. sought to improve the resin portion of the epoxy polymer system and, in doing so, they prepared a series of aromatic glycidyl ethers with fluorinated side chains (see, Griffith, J. R., et al., *CHEMTECH* 311 (1972);

Griffith, J. R., et al., CHEMTECH 290 (1982); U.S. Pat. No. 3,879,430 which issued Apr. 22, 1995. to J. G. O'Rear; and U.S. Pat. No. 4,157,358 which issued Jun. 5, 1979 to Field, D. E., et al. When such fluorinated resins are cured with commercial hardeners, epoxy polymers with improved water repellency characteristics are obtained. However, most of the hardeners currently available are designed for hydrocarbon or aromatic epoxies and, thus, are not miscible with fluorinated materials. Consequently, fluorinated epoxies with optimum surface and mechanical properties cannot be prepared. Moreover, curing agents that contain fluorine, such as the fluorinated diamines previously prepared by Malik, et al. (J. Org. Chem., 56: 3043 (1991)), are miscible with highly fluorinated glycidyl ethers, but due to their low nucleophilicity, react poorly with glycidyl ethers to give materials with poor properties. As such, a need exists for a curing agent which is miscible with fluorine-containing materials and which will react readily with electrophiles, e.g., fluorinated glycidyl ethers.

The present invention provides fluorinated diamines which can be used as curing agents with fluorinated glycidyl ethers to form fluorinated epoxy polymers. Moreover, the fluorinated diamines of this invention can also be used as curing agents with commercially available non-fluorinated aromatic glycidyl ether resins. In the fluorinated diamines of the present invention, fluorine is in the side chain and is, thus, substantially removed from the amine end groups. As such, the fluorinated diamines of the present invention readily react with fluorinated glycidyl ethers and with commercially available non-fluorinated aromatic glycidyl ethers. Moreover, as a result of the presence of fluorine in the side chains, the fluorinated diamines of the present invention are completely miscible with fluorinated glycidyl ethers in all proportions. Surprisingly, the fluorinated diamines of this invention are also completely miscible with non-fluorinated glycidyl ethers, including, for example, the aromatic glycidyl ether resin which is commercially available from DOW Chemical Co. under the tradename DER 331*. In addition, due to the high miscibility of the fluorinated diamines with both fluorinated glycidyl ethers and non-fluorinated aromatic glycidyl ethers, the resulting epoxy polymers are optically clear and, thus, can be used as optical materials.

As such, in another aspect, the present invention provides a process for the preparation of a fluorinated, cross-linked epoxy polymer, the process comprising: (a) mixing a glycidyl ether resin with a fluorinated diamine to form a mixture; (b) casting the mixture into a mold; (c) de-gassing the cast mixture; and (d) curing the cast mixture at a temperature of between about 0° C. and 120° C. The fluorinated diamine used in this process has the general formula

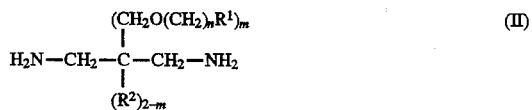

As previously described, in Formula II, $R^1$ is a functional group including, but not limited to, the following: linear and branched chain perfluoroalkyls, having from 1 to about 20 carbon atoms; omega-hydroperfluoroalkyls, having from 1 to about 20 carbon atoms; and oxa-perfluorinated polyethers, having from 4 to about 60 carbon atoms. $R^2$ is a functional group including, but not limited to, lower alkyls having from 1 to 4 carbon atoms. The index "m" represents an integer having a value of 1 or 2. The index "n" represents an integer having a value ranging from 1 to about 10.

In the above process, the mixture is cured at a temperature ranging from 0° C. to about 120° C. and, more preferably, at a temperature ranging from 50° C. to about 70° C. At room temperature, the rate of cure is relatively slow and can be accelerated by adding a catalyst. However, at higher temperature, the cure is extremely fast and can be conducted in the absence of a catalyst. As such, the curing step can be carded out in the presence or absence of a catalyst. If a catalyst is used, suitable catalysts include, but are not limited to, weak acids, such as acetic acid, or weak bases, such as 1,4-diazabicyclo [2.2.2]octane (DABCO). Suitable glycidyl ether resins include, but are not limited to, bisphenol A epoxies, hydrogenated bisphenol A epoxies, 2,2-bis[4-(3-n-butoxy-2-glycidyloxy-1-propoxy)phenyl] propane, triglycidylisocyanurate and fluorinated glycidyl ether resins having the general structure:

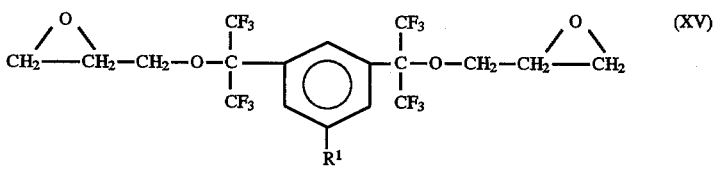

In the formula, $R^1$ is a functional group having the general formula $-(CF_2)_x-CF_3$, wherein the index "x" is an interger having a value ranging from 2 to about 10. Typically, the ratio of fluorinated diamine to glycidyl ether ranges from about 0.8:1.0 to about 1.2:1.0, but fluorinated, cross-linked epoxy polymers with optimal mechanical properties are obtained when a ratio approaching 1:1 is employed.

The fluorinated epoxy polymers prepared using the fluorinated diamines of the present invention have improved properties and, as such, are useful as potting compounds for electronic equipment or other equipment that needs protection from moisture, submarine antenna coatings, seals for chemical storage tanks, underwater hull coatings, and a variety of dental and medical applications (artificial joints).

This invention will be described in greater detail by way of specific examples. The following examples are offered for illustrative purposes, and are intended neither to limit or define the invention in any manner.

GENERAL EXPERIMENTAL METHODOLOGY $^1$H, $^{13}$C and $^{19}$F NMR analyses were conducted on a 300 MHz Bruker MSL-300 spectrometer. Proton and carbon chemical shifts are reported in parts per million (ppm) relative to tetramethylsilane. Fluorine chemical shifts are reported in parts per million relative to trichlorofluoromethane. Infrared analyses were conducted on a Nicolet SX-5 spectrometer. Gel permeation chromatography (GPC)

was conducted on a Water's gel permeation chromatograph equipped with four ultrastyragel columns (100 Å, 500 Å, $10^3$ Å and $10^4$ Å), a differential refractive index detector and a Data Module 730. THF was used as the mobile phase. The GPC was calibrated with a series of well-characterized (i.e., $M_n$ and $M_w$ are well known) polystyrene standards (Narrow Standards), and thus the number average molecular weight ($M_n$) and weight average molecular weight ($M_w$) reported are expressed relative to polystyrene. Elemental analysis was conducted by Galbraith Laboratories in Knoxville, Tenn. Equivalent weights were determined by $^1$H NMR employing trifluoroacetic anhydride (TFAA) end group analysis. Mechanical properties (Stress-Strain analysis) were measured with a Model 1122 Instron tester. Static contact angles of water with the polymer surface were measured with a Goniometer using doubly distilled water. Differential scanning calorimetry (DSC) and Thermogravimetric Analysis (TGA) were performed on a DuPont 990 thermal analyzer system. DSC measurements were made at a heating rate of 10° C./min in air, whereas TGA measurements were made at a heating rate of 20° C./min in air at a flow rate of 20 mL/min.

Fluoroalcohols were purchased commercially from either 3M Corporation or DuPont Corporation, and, with the exception of DuPont's Zonyl BA-L alcohols, were used as received. Purification of the Zonyl BA-L alcohols is described in Example III. Isocyanates, such as isophorone diisocyanate (IPDI), saturated methylenediphenyl diisocyanate (Des-W), N-100 and N3200, were obtained from Mobay Chemical Co. Isopherone diisocyanate (IPDI) was distilled prior to polymerization.

EXAMPLE I

This example illustrates the preparation and properties of 3-(2,2,3,3,4,4,4-heptafluorobutoxymethyl)-3-methyloxetane (7-FOX).

A 50 weight percent dispersion of sodium hydride (6.1 grams, 127 mmol) in mineral oil, was washed twice with hexanes and was suspended in 60 milliliters of dimethyl formamide. Then 24.0 grams (120 mmol) of 2,2,3,3,4,4,4-heptafluorobutan-1-ol was added and the mixture was stirred for 45 minutes. A solution of 25.0 grams (97.5 mmol) of 3-hydroxymethyl-3-methyloxetane p-toluenesulfonate in 15 milliliters of dimethyl formamide was added and the mixture was heated at 75°–85° C. for 30 hours when $^1$HNMR analysis of an aliquot showed that the starting sulfonate had been consumed.

The mixture was poured into 100 milliliters of ice/water and extracted with two volumes of methylene chloride. The combined organic extracts were washed twice with water, twice with 2 weight percent aqueous hydrochloric acid, brine, dried over magnesium sulfate, and evaporated to give 27.5 grams of 3-(2,2,3,3,4,4,4-heptafluorobutoxymethyl)-3-methyloxetane (i.e., 7-FOX) as an oil. The oil was distilled at 33° C. and 0.2 millimeters mercury pressure to give 12.2 grams of analytically pure ether, corresponding to a 44 percent yield. The experimental analyses were: IR (KBr) 2960–2880, 1280–1030, 995, 840 cm$^{-1}$, $^1$H δ NMR 1.31 (s, 3H), 3.67 (s 2H), 3.99(t, J=13.3 Hz, 2H), 4.34 (d, J=5.7 Hz 2H), 4.50 (d, J=5.7 Hz, 2H); $^{13}$C NMR δ 20.242, 39.627, 67.778, 77.730, 79.110, 108.72, 114.7, 117.58; $^{19}$F NMR δ −81.4, −120.6, −128.1. The calculated elemental analysis for $C_9H_{11}F_7O_2$ is C=38.04; H=3.90; F=46.80. The experimental analyses found: C=38.03; H=3.65; and F=46.59.

EXAMPLE II

This example illustrates the preparation and properties of 3,3-bis(2,2,3,3,4,4,4-heptafluorobutoxymethyl)-3-methyloxetane (14-FOX).

In a manner similar to that described above, 3,3-bis (chloromethyl) oxetane (155 g, 1 mole) was reacted with 2,2,3,3,4,4,4-heptafluorobutan-1ol (402 g, 2.01 moles) in DMF (2 L) in the presence of sodium hydride (100 g of 50% dispersion in mineral oil, 2.3 moles) at 85° C. for 16 h to give 340 g (70%) of 3,3-bis(2,2,3,3,4,4,4-heptafluorobutoxymethyl) oxetane, a clear, colorless liquid. Glc analysis revealed the purity of this material to be in excess of 99%: BP=70°–72° C./1.0–1.3 mm-hG; $^1$H NMR (CDCl$_3$) δ 4.44 (s, 4H), 3.97 (t, J=13.2 Hz), 3.86 (s, 4H); $13_c$ NMR δ 43.9, 68.1 (t), 73.5, and 75.6 (Signals from carbons bearing fluorine are not included due to the complex splitting patterns and overlap of signals); $19_f$NMR δ −81.6 (3 F), −121.0 (2 F) and −128.3 (2 F); Anal. Calcd for $C_{13}H_{12}F_{14}O_3$: C, 32.4; H, 2.5. Found: C, 32.3; H, 2.3.

EXAMPLE III

This example illustrates the purification of commercial fluoroalcohols.

Zonyl BA-L is a narrow distribution, oligomeric mixture of fluoroalcohols that is available from Dupont Chemicals in pilot plant quantities. Zonyl BA-L is a yellow liquid which by GLC is a mixture of the following oligomers: 3-(3,3,4,4,5,5,6,6,7,7,8,8,8-tridecafluorooctan-1-ol (C8, 60%); 3,3,4,4,5,5,6,6,7,7,8,8,9,9,10,10,10-heptadecafluorodecan-1-ol (C10, 26%); 3,3,,4,4,5,5,6,6,7,7,8,8,9,9,10,10,11,11,12,12,12-heneicosafluorododecanol (C 12, 6%); and various unidentified high boiling compounds (8%). Zonyl BA-L was washed with equal volumes of 10 weight percent aqueous sodium thiosulfate, 10 weight percent aqueous sodium bicarbonate (to remove HF), water and brine, dried, filtered, and distilled under reduced pressure (3 mm-Hg) at 50°–100° C. to give a mixture of 69% C8, 26% C10 and 5% C12 in 83% yield.

EXAMPLE IV

This example illustrates the preparation and properties of 3,3,4,4,5,5,6,6,7,7,8,8,8-tridecafluorooctyloxymethyl-, 3,3,4,4,5,5,6,6,7,7,8,8,9,9,10,10,10-heptadecafluorododecyloxymethyl-, and 3,3,4,4,5,5,6,6,7,7,8,8,9,9,10,10,11,11,12,12,12-heneicosafluorododecyloxymethyl-3-methyloxetane.

In a manner similar to that described in Example I, a mixture of 69% C8, 26% C10 and 5% C12 fluoroalcohols (distilled Zonyl BA-L from Example B5, 51.6 grams, 129 mmol) was reacted with 27 grams of 3-iodomethyl-3-methyloxetane (127 mmol) in 500 milliliters of dimethylformamide at 85° C. for 18 hours to give 60 grams of crude product. The crude product was fractionally distilled through a 6" Vigerux column to yield the following fractions: Fraction #1 (4.8 grams) was collected between 25° C. and 45° C. at 3.5–2.9 mm-Hg, and was a mixture of unreacted fluoroalcohols. Fraction #2 (2.8 grams) was collected at 45°–71° C./0.7–3.0 mm-Hg, and was a mixture of unreacted fluoroalcohols and fluorinated oxetane monomers. The final fraction (49 grams, 80%), boiling at 70°–85° C./0.7–0.9 mm-Hg, was a mixture of 73% 3,3,4,4,5,5,6,6,7,7,8,8,8-tridecafluorooctyloxymethyl-3-methyloxetane (13-FOX), 24% 3,3,4,4,5,5,6,6,7,7,8,8,9,9,10,10,10-heptadecafluorodecyloxymethyl-3-methyloxetane (17-FOX), and 3% 3,3,4,4,5,5,6,6,7,7,8,8,9,9,10,10,11,11,12,12, 12-heneicosafluorododecyloxymethyl-3-methyloxetane (21-FOX), a colorless oil with a boiling point of 70°–85° C./0.7–0.9 mm-Hg; $^1$H NMR (CDCl$_3$) δ 4.50 and 4.35 (AB, J=5.9 Hz, 4H),3.78 (t, J=6.6 Hz, 2H), 3.53 (s, 2H), 2.42 (t, J=6.6 and 17.6 Hz, 2H), and 1.31 (s, 3H); $^{13}$C NMR δ 21.3, 31.86 (t, J=130.1 Hz), 40.2, 63.6, 76.8, and 80.2 (signals for carbons bearing fluorine are not included due to complex splitting patterns and overlap of signals; $^{19}$F NMR δ –81.5, –113.8, –122.3, –123.3, –124.1, –124.5, –125.8, and 126.7.

EXAMPLE V

This example illustrates the preparation and properties of 3-bromo-2-heptafluorobutoxymethyl-2-methyl-1-propanol.

A 2-L, 3-neck, jacketed flask fitted with a mechanical stirrer, thermocouple probe, and an addition funnel was charged with 48% hydrobromic acid (208.0 g, 1.23 mole). The flask was cooled to 5° C. by circulating coolant through the jacket, and 3-heptafluorobutoxymethyl-3-methyloxetane was added at a rate to maintain the temperature below 12° C. The addition was complete after 1¼ hours. GC analysis indicated 98% conversion of the starting material to product. Additional 48% HBr (14.9 g, 0.088 mole) was added, and the mixture was stirred overnight at room temperature. The mixture was poured into 200-ml water, and the pH of the aqueous layer was adjusted to a pH of about 5 with 1N NaOH. The layers were separated, and the organic layer was washed with water (250 ml), dried (MgSO$_4$), and filtered to give 300.4 g (93.5%) of 3-bromo-2-heptafluorobutoxymethyl-2-methyl-1-propanol (2), a clear oil: $^1$H NMR (CDCl$_3$) 1.00 (s), 3.43 and 3.52 (AB, J=10.4 Hz), 3.53 and 3.59 (AB, J=11.1 Hz), 3.58 (s), and 3.95 (t, J=13.4 Hz); Anal. Calcd for C$_9$H$_{12}$BrF$_7$O$_2$: C, 29.60; H, 3.32; Br, 21.88; Found: C, 29.15; H, 3.27; Br, 21.09.

EXAMPLE VI

This example illustrates the preparation and properties of 3-bromo-2,2-bis(heptafluorobutoxymethyl)-1-propanol.

In a manner similar to that described above, 3,3-bis (heptafluorobutoxymethyl)oxetane (250.0 g, 0.52 mole) was reacted with 48% HBr (131.7 g, 0.78 mole) to give 260.9 g (89.1%) of 3-bromo-2,2-bis(heptafluorobutoxymethyl)-1-propanol, a clear oil: $^1$H NMR (CDCl$_3$) 3.49 (s, 2H), 3.65 (s, 4H), 3.69 (s, 2H), and 3.95 (t, J=13.3 Hz, 2H); Anal. Calcd for C$_{13}$H$_{13}$BrF$_{14}$O$_3$: C, 27.72; H, 2.33; Br, 14.19; Found: C, 27.73; H, 2.27; Br, 14.09.

EXAMPLE VII

This example illustrates the preparation and properties of 3-bromo-2-heptafluorobutoxymethyl-2-methyl-1-propanol mesylate.

A 2-L, 4-necked flask fitted with a mechanical stirrer, thermocouple probe, and a 250-ml addition funnel was charged with 3-bromo-2-heptafluorobutoxymethy-2-methyl-1-propanol (300.4 g, 0.82 mole), triethylamine (94.9 g, 0.94 mole), and methylene chloride (480 ml). The flask was cooled in an ice bath and a solution of methanesulfonyl chloride (106.0 g, 0.93 mole) in methylene chloride (200 ml) was added at a rate to maintain the temperature below 8° C. The addition was complete after one hour. GC analysis indicated that about 32% of the starting material remained unreacted. Additional triethylamine (30.5 g, 0.30 mole) and methanesulfonyl chloride (14.8 g, 0.13 mole) were added, and the mixture was stirred for one hour. The mixture was poured into ice water (1000 ml), and the organic layer was separated and washed with water (3×800 ml). The organic phase was dried (MgSO$_4$), filtered, and stripped of solvent on a rotary evaporator to give 347.0 g (95.8%) of 3-bromo-2-heptafluorobutoxymethyl-2-methyl-1-propanol (3), a yellow-orange oil: IR 2981, 2950, 1340, 1220, 1175, and 1120 cm$^{-1}$; $^1$H NMR (CDCl$_3$) 1.13 (s, 3H), 3.00 (s, 3H), 3.4(s, 2H), 3.56 (s, 2H), 3.97 (t, J=13.3 Hz, 2H), and 4.14 (s, 2H); $^{13}$C NMR (CDCl$_3$) 17.97, 36.57, 36.89, 40.07, 68.04 (t, J=26.19), 71.40, and 74.53. Anal. Calcd for C$_{10}$H$_{14}$BrF$_7$O$_4$S : C, 27.09; H, 3.20; Br, 18.03; F, 30.01; Found: C,27.01; H, 3.20; Br, 18.21.

EXAMPLE VIII

This example illustrates the preparation and properties of 3-bromo-2,2-bis-(heptafluorobutoxymethyl)-1-propanol mesylate.

In a manner similar to that described above, 3-bromo-2, 2-bis-(heptafluorobutoxymethyl)-1-propanol (250.0 g, 0.44 mole) was reacted with methanesulfonyl chloride (58.45 g, 0.51 mole) and triethylamine (52.62 g, 0.52 mole) in methylene chloride (400+200 ml). Additional methanesulfonyl chloride (2.96 g, 0.03 mole) was added to bring the reaction to completion. Washing and removal of the solvent gave 268.4 g (95.2%) of 3-bromo-2,2-bis (heptafluorobutoxymethyl)-1-propanol mesylate (4), a yellow oil: IR 2940, 1350, 1223, 1176, and 1120 cm$^{-1}$; $^1$H NMR (CDCl$_3$) 3.02 (s, 3H), 3.49 (s, 2H), 3.68 (s, 4H), 3.97 (t, J=13.3 Hz, 4H), and 4.24 (s, 2H); $^{13}$C NMR (CDCl$_3$) 31.66, 36.64, 44.60, 67.81 (t, J=26.44), 68.36, and 70.30. Anal. Calcd for C$_{14}$H$_{15}$BrF$_{14}$O$_5$S: C, 26.22; H, 2.36; Br, 12.46, F, 41.48. Found: C, 25.95; H, 2.33; Br, 12.88.

EXAMPLE IX

This example illustrates the preparation and properties of 1,3-diazido-2-heptafluorobutoxymethyl-2-methyl-propane.

A mixture of 3-bromo-2-heptafluorobutoxymethyl-2-methyl-1-propanol mesylate (280.0 g, 0.63 mole), sodium azide (113.3 g, 1.74 mole) and dimethylformamide (1.1 L) was heated in a 2-L, 3-necked flask at 110° C. for 48 hours. The progress of the reaction was monitored by GLC. On completion, the reaction mixture was cooled to room temperature and poured into 3 L of water. The organic phase was separated, and the aqueous phase was extracted with diethyl ether (2×250 ml). The extracts were combined with the organic phase and washed water (2×300 ml), 0.5% HCl (300 ml), and brine (300 ml). The organic phase was dried over magnesium sulfate, filtered and stripped of solvent on a rotary evaporator to give 202.7 g (91.0%) of 1,3-diazido-2-heptafluorobutoxymethyl-2-methyl-propane, a yellow oil: IR 2980, 2950, 2895, 2110 (—N$_3$), 1342, 1230, 1185, and 1124 cm$^{-1}$; $^1$H NMR (CDCl$_3$) 0.93 (s, 3H), 3.28 (s, 4H), 3.42 (s, 2H), and 3.96 (t, J=13.3, 2H); $^{13}$C NMR 17.95, 41.01, 55.27, 68.03 (t, J=26.59 Hz), and 75.01. Anal. Calcd for C$_9$H$_{11}$F$_7$N$_6$O: C, 30.68, H, 3.15; F, 37.76; N, 23.86; Found: C, 30.75; H, 3.17; N, 23.27.

EXAMPLE X

This example illustrates the preparation and properties of 1,3-diazido-2,2-bis(heptafluorobutoxymethyl)-propane.

In a manner similar to that described above, 3-bromo-2, 2-bis-(heptafluorobutoxymethyl-1-propanol mesylate (243.15 g, 0.379 mole) was reacted with sodium azide 68.3 g, 1.05 mole) in dimethylformamide (750 ml) to give 201.7 g (96.7%) of 1,3-diazido-2,2-bis(heptafluorobutoxymethyl) propane, a yellow oil: IR: 2940, 2890, 2100 (—N$_3$), 1338, 1290, 1225, and 1117 cm$^{-1}$; $^1$H NMR (CDCl$_3$) 3.37 (s, 4H).

3.51 (s, 4H), and 3.92 (t, J=13.2 Hz, 4H); $^{13}$C NMR (CDCl$_3$) 45.22, 50.77, 68.04 (t, J=26.47 Hz), and 70.76; Anal. Calcd for C$_{13}$H$_{12}$F$_{14}$N$_6$O$_2$: C, 28.37, H, 2.20; F, 48.34; N, 15.28; Found: C, 28.78; H, 2.26; N, 14.97.

EXAMPLE XI

This example illustrates the preparation and properties of 1,3-diamino-2- heptafluorobutoxymethyl-2-methyl-propane.

1,3-Diazido-2-heptafluorobutoxymethyl-2-methyl-propane (50.0 g, 0.142 mole) was weighed into a 1-L, 3-neck flask fitted with a magnetic stir bar, reflux condenser, drying tube and a thermocouple probe. Pearlman's catalyst (4.2 g, 10% Pd on carbon) was slurried in methanol (50 ml) and added to the flask. The mixture was stirred, and additional methanol (200 ml) was added. After heating to 60° C., anhydrous hydrazine (5.0 g, 0.16 mole) was added with a syringe at a rate such that the temperature did not exceed 63° C. Evolution of gas was observed during the addition, and the addition was complete after 20 minutes. $^1$H NMR analysis indicated that the reaction was 80% complete. A second portion of anhydrous hydrazine (1.27 g, 0.04 mole) was added, and the mixture was stirred overnight at 60° C. The progress of the reaction was also monitored by GC and by following the disappearance of the N$_3$ stretching band in the infrared spectrum. The mixture was cooled to room temperature, filtered, and stripped of solvent on a rotary evaporator. Short path distillation of the crude product (bp 45°–47° C., high vacuum) gave 36.1 g (84.7%) of 1,3-diamino-2-heptafluorobutoxymethyl-2-methyl-propane (9), a clear oil: IR 3400–3370 (NH$_2$), 2925, 2875, 1330, 1225, and 1120 cm$^{-1}$; $^1$H NMR (CDCl$_3$) 0.84 (s, 3H), 1.20 (s, 4H), 2.63 (s, 4H), 3,46 (s, 2H) and 3.92 (t, J=13.8 Hz, 2H); $^{13}$C NMR (CDCl$_3$) 18.36, 40.27, 46.85 68.38 (t, J=25.92 Hz), and 77.72. Anal. Calcd for C$_9$H$_{15}$F$_7$N$_2$: C, 36.00; H, 5.05; N, 9.33; Found: C, 34.99; H, 5.08; N, 7.98.

H. EXAMPLE XII

This example illustrates the preparation and properties of 1,3-diamino-2,2-bis(heptafluorobutoxymethyl)-propane.

In a manner similar to that described above, 1,3-diazido-2,2-bis(heptafluorobutoxymethyl)propane (50.0 g, 0,091 mole) was reacted with anhydrous hydrazine (3.64g, 0.11 mole) in the presence of Pearlman's catalyst (10% Pd/C, 2.70 g) and methanol (225 ml). Filtration and removal of the methanol on a rotary evaporator gave 40.26 g (88.8%) of the crude product. A portion of the product was short-path distilled (74°–75° C./0.2 mm-Hg) to give a clear oil (12.5 g, 72%): IR 3420–3200 (NH$_2$), 2940, 2895, 1340, 1228, and 1123; $^1$H NMR (CDCl$_3$) 1.14 (s, 2H), 2.69 (s, 2H, 3.55 (s, 2H), and 3.91 (t, J=13.8 Hz, 2H; $^{13}$C NMR 42.39 (t, J =4.45 Hz), 44.68, 68.10 (t, J=26.36 Hz), and 73.20. Anal. Calcd for C$_{13}$H$_{16}$F$_{14}$N$_2$O$_2$ : C, 31.33; H, 3.24; N, 5.62; Found: C, 30.89; H, 3.20; N, 4.98.

EXAMPLE XIII

This example illustrates the preparation and properties of a mixture of 3,3,4,4,5,5,6,6,7,7,8,8,8-tridecafluorooctyloxymethyl-, 3,3,4,4,5,5,6,6,7,7,8,8,9,9,10,10,10-heptadecafluorododecyloxymethyl-, and 3,3,4,4,5,5,6,6,7,7,8,8,9,9,10,10,11,11,12,12,12-heneicosafluorododecyloxymethyl-3-bromo-2-methyl-1-propanol.

A mixture of 69% 3-(3,3,4,4,5,5,6,6,7,7,8,8,8-tridecafluorooctyl-oxymethyl)-3-methyloxetane (13-FOX), 26% 3-(3,3,4,4,5,5,6,6,-7,7,8,8,9,9,10,10,10-heptadecafluorododecyloxymethyl-3-methyloxetane (17-FOX), and 5% 3-(3,3,4,4,5,5,6,6,-7,7,8,8,9,9,10,10,11,11,12,12,12-heneicosafluorododecyl-oxymethyl)-3-methyloxetane (21-FOX) (20.0 g, 41.3 mmol) was added to 48% aqueous HBr (15g, 90 mmol) at room temperature. The mixture was stirred at room temperature for 16 h, at which point $^1$H NMR analysis of an aliquot indicated total consumption of the starting oxetanes. The reaction mixture was then slowly added to water, and the bottom layer was dissolved in Freon 113 and washed with water (2×). The organic layer was added over magnesium sulfate (MgSO$_4$), filtered and stripped of solvent under reduced pressure to give 21.1 g (90.5%) of the title product, a pale yellow oil. GLC analysis revealed that the crude product was about 95% pure. The crude product was used without further purification in the next reaction: $^1$H NMR 1.03 (s, 3H), 2.35 (m, 2H), 3.41 (AB, 2H), 3.54 (AB, 2H), 3.60 (s, 2H), and 3.86 (t, 2H).

EXAMPLE XIV

This example illustrates the preparation and properties of a mixture of 3,3,4,4,5,5,6,6,7,7,8,8,8-tridecafluorooctyloxymethyl-, 3,3,4,4,5,5,6,6,7,7,8,8,9,9,10,10,10-heptadecafluorododecyloxymethyl- and 3,3,4,4,5,5,6,6,7,7,8,8,9,9,10,10,11,11,12,12,12-heneicosafluorododecyloxymethyl- 3-bromo-2-methyl-1-propanol mesylate.

A solution of methanesulfonyl chloride (4.61 g, 40.3 mmol) in methylene chloride (15 mL) was added to a solution of 3,3,4,4,5,5,6,6,7,7,8,8,8-tridecafluorooctyloxymethyl-, 3,3,4,4,5,5,6,6,7,7,8,8,9,9,10,10,10-heptadecafluorodecyloxymethyl-, and 3,3,4,4,5,5,6,6,7,7,8,8,9,9,10,10,11,11,12,12,12-heneicosafluorododecyloxymethyl-3-bromo-2-methyl-1-propanol (20 g, 35.5 mmol) and triethylamine (4.67 g, 46.3 mmol) in methylene chloride (30 mL) at room temperature.

During addition, precipitation of a white solid was observed. The progress of the reaction was monitored by GLC, and when the starting material was completely consumed, methylene chloride was added and the mixture was quenched in ice/water. The organic phase was separated, washed with water (2×), dried over magnesium sulfate (MgSO$_4$), filtered and stripped of solvent under reduced pressure to give 20.1 g (89%) of the title product, a yellow oil. GLC analysis revealed that the product was about 97% pure: $^1$H NMR 1.12 (s, 3H), 2.36 (m, 2H), 3.03 (s, 3H), 3.45 (m, 4H), 3.75 (t, 2H), and 4.15 (s, 2H); $^{13}$C NMR 72.93, 71.88, 63.30, 39.90, 37.15, 36.90, 31.3 (t), and 18.16 (signals from carbon bearing fluorine are not included).

EXAMPLE XV

This example illustrates the preparation and properties of a mixture of 3,3,4,4,5,5,6,6,7,7,8,8,8-tridecafluorooctyloxymethyl-, 3,3,4,4,5,5,6,6,7,7,8,8,9,9,10,10,10-heptadecafluorododecyloxymethyl-, and 3,3,4,4,5,5,6,6,7,7,8,8,9,9,10,10,11,11,12,12,12-heneicosafluorododecyloxymethyl-1,3-diazido-2-methyl-propane.

A mixture of 3,3,4,4,5,5,6,6,7,7,8,8,8-tridecafluorooctyloxymethyl-, 3,3,4,4,5,5,6,6,7,7,8,8,9,9,10,10,10-heptadecafluorododecyloxymethyl- and 3,3,4,4,5,5,6,6,7,7,8,8,9,9,10,10,11,11,12,12,12-heneicosafluorododecyloxymethyl-3-bromo-2-methyl-1-propanol mesylate (18 g, 28.0 mmol), sodium azide (5.02 g, 77.3 mmol), and dimethylformamide (30 mL) was heated in a round bottom flask at 110° C. for 48 h. The progress of the reaction was monitored by GLC and $^1$H NMR. On completion, the reaction mixture was cooled to room temperature and poured into 500 mL of water. The organic layer was separated and the aqueous layer was extracted with diethyl ether (2×50 mL). The ethereal extracts were combined with the organic phase and washed with water (2×100 mL), 0.5 N HCl (100 mL), and brine (100 mL). The organic phase was then dried over magnesium sulfate (MgSO$_4$), filtered, and stripped of solvent under reduced pressure to give 14.4 g (93%) of the title product, a yellow oil: IR 2980, 2945, 2115 (N$_3$), 1350, 1225, 1185, and 1120 cm$^{-1}$; $^1$H NMR 0.95 (s, 3H), 2.35 (m, 2H), 3.30 (s, 4H), 3.40 (s, 2H), and 3.73 (t, 2H).

EXAMPLE XVI

This example illustrates the preparation and properties of a mixture of 3,3,4,4,5,5,6,6,7,7,8,8,8-tridecafluorooctyloxymethyl-, 3,3,4,4,5,5,6,6,7,7,8,8,9,9,10,10,10-heptadecafluorododecyloxymethyl-, and 3,3,4,4,5,5,6,6,7,7,8,8,9,9,10,10,11,11,12,12,12-heneicosafluorododecyloxymethyl-1,3-diamino-2-methyl-propane.

A 3-necked round bottom flask fitted with a reflux condenser, nitrogen inlet/outlet ports, thermometer and a magnetic stirring bar was charged with a mixture of 3,3,4,4,5,5,6,6,7,7,8,8,8-tridecafluorooctyloxymethyl-, 3,3,4,4,5,5,6,6,7,7,8,8,9,9,10,10,10-heptadecafluorododecyloxymethyl-, and 3,3,4,4,5,5,6,6,7,7,8,8,9,9,10,10,11,11,12,12,12-heneicosafluorododecyloxymethyl-1,3-diazido-2-methyl-propane (10 g, 18.1 mmol), methanol (30 mL), and Pearlman's catalyst (1 g, 10% Pd on carbon). The mixture was stirred at room temperature for 10 minutes and then heated to 60° C. Next, a solution of anhydrous hydrazine (1.0 g, 31.2 mmol) in methanol (5 mL) was added in a manner such that the reaction temperature did not exceed 65° C. Evolution of a gas was observed and the mixture was heated at 60° C. for 16 h. $^1$H NMR of an aliquot indicated that the reaction was about 87% complete. A second portion of anhydrous hydrazine (0.3 g) was added, and the mixture was heated at 60° C. for an additional 4 h. The progress of the reaction was also monitored by following the disappearance of the N$_3$ stretching band in the infrared spectrum. On completion, the reaction was cooled to room temperature, filtered, and stripped of solvent under reduced pressure to give 8.9 g of the crude product. Bulb-to-bulb distillation of the crude product under reduced pressure (120° C./1 mm-Hg) afforded 6.8 g (75%) of the tire product, a colorless oil. GLC analysis revealed the product was greater than 98% pure and consisted of 75% 3,3,4,4,5,5,6,6,7,7,8,8,8-tridecafluorooctyloxymethyl- 1,3-diamino-2-methyl-propane (13-FDA), 23% 3,3,4,4,5,5,6,6,7,7,-8,8,9,9,10,10,10-heptadecafluorodecyloxymethyl-1,3-diamino-2-methyl-propane (17-FDA), and 2% 3,3,4,4,5,5,6,6,7,7,8,8,9,9,10,10,11,11,12,12,12-heneicosafluorododecyloxymethyl-1,3-diamino-2-methyl-propane (21-FDA): IR 3400 (N—H), 2935, 1335, 1225, and 1120 cm$^{-1}$; $^1$H NMR 0.85 (s, 3H), 1.18 (brs, 4H, exchanges with D$_2$O), 2.34 (m, 2H), 2.65 (s, 4H), 3.42 (s, 2H), and 3.76 (t, 2H); $^{13}$C NMR 73.1, 71.9, 54.9, 40.9, 31.8, and 18.1 (signals from carbon bearing fluorine are not included).

I EXAMPLE XVII

This example illustrates the preparation and properties of polyurea from 1,3-diamino-2-heptafluorobutoxymethyl-2-methyl-propane and Desmodur W.

A 3-necked, 25 ml round bottomed flask fitted with a magnetic stirring bar, rubber septums, and a nitrogen inlet/outlet was dried with a heat gun, cooled to room temperature under nitrogen, and charged with Desmodur-W (trade name for HMDI, 0.90 g, 6.70 meq.) and 1 ml of anhydrous THF. Next, a solution of freshly distilled 1,3-diamino-2-heptafluorobutoxymethyl-2-methyl-propane (100 g, 6.67 meq.) in anhydrous THF (0.5 ml) was added to the reaction mixture dropwise via a syringe. An exothermic reaction accompanied by precipitation of the polyurea was observed. The mixture was stirred at room temperature until it became too viscous to stir. At this point, the solvent was evaporated and the polymer, a white powdery material, was removed from the flask and dried in an oven at 50° C./0.5 mm-Hg for 1 hour. The polymer was soluble in DMF, DMSO and sulfuric acid, but was insoluble in chloroform, toluene, acetone and THF. The polymer exhibited an onset of major degradation in air (TGA) at 327° C. The inherent viscosity of this polymer (measured in DMF at 0.5 g/dL concentration at 25° C.) was 0.18 dL/g.

J. EXAMPLE XVIII

This example illustrates the preparation and properties of polyurea from 1,3-diamino-2-heptafluorobutoxymethyl-2-methyl propane and Isopherone Diisocyanate.

In a manner similar to that described above, 1,3-diamino-2-heptafluorobutoxymethyl-2-methylpropane (0.506 g, 3.37 meq.) was reacted with IPDI (0.383 g, 3.37 meq.) in anhydrous THF (2 ml) to give 0.84 g of polyurea, a white powdery material. The polymer was soluble in DMF, THF, DMSO and sulfuric acid, but was insoluble in acetone, Freon 113, toluene and chloroform. The inherent viscosity of the polymer (measured in DMF at a concentration of 0.50 g/dL at 25° C.) was 0.16 dL/g. The polymer exhibited an onset of major thermal degradation in air at 318° C.

K. EXAMPLE XVIV

This example illustrates the preparation and properties of polyurea from 1,3-diamino-2,2-bis(heptafluorobutoxymethyl)propane and Desmodur W.

In a manner similar to that described above, 1,3-diamino-2,2-bis(heptafluorobutoxymethyl)propane (1.00 g, 4.0 meq.) was reacted with Desmodur-W (0,541 g, 4.0 meq) in THF (2 ml) at room temperature to give 1.4 g of the desired polyurea, a white powdery material. The polymer was soluble in DMF, acetone, THF, DMSO and sulfuric acid, but was insoluble in Freon 113, toluene, and chloroform. The inherent viscosity of the polymer (measured in DMF at a concentration of 0.50 g/dL at 25° C.) was 0.14 dL/g. The polymer exhibited an onset of major thermal degradation in air at 323° C.

EXAMPLE XX

This example illustrates the preparation and properties of an epoxy from 1,3-diamino-2-heptafluorobutoxymethyl-2-methylpropane (7-FDA) and D.E.R. 331.

A mixture of 1,3-diamino-2-heptafluorobutoxymethyl-2-methylpropane (510 mg, 3.40 meq), D.E.R. 331 (629.3 mg, 3.40 meq, sample from DOW chemicals), and one drop of a catalyst solution consisting of a 1:1 mixture of dibutyltin dilaurate and DASCO in THF was hand mixed in a poly beaker and cured at 60° C. for 16 h. The resulting polymer, a tack-free, transparent glass was removed from the mold and characterized by contact angle analysis. The contact angle of this material with doubly distilled water was 98°.

D.E.R. 331 is a commercial epoxy resin available from DOW Corning Inc., and is a mixture of oligomers of glycidyl ether of Bisphenol-A.

EXAMPLE XXI

This example illustrates the preparation and properties of an epoxy from 1,3-diazido-2,2-bis (heptafluorobutoxymethyl)-propane (14-FDA__ and D.E.R. 331.

In a manner similar to that described above, 14-FDA (2.1 g, 8.43 meq) was reacted with DER 331 (1.66 g, 8.43 meq) in the presence of a catalyst (1:1 mixture of Dabsco* and dibutylin dilaurate, 12 mg) at 50° C. for 16 h to give a tack-free, transparent plastic. The contact angle of this material with doubly distilled water was 110°.

EXAMPLE XXII

This example illustrates the preparation and properties of a polyimide from 1,3-diamino-2-heptafluorobutoxymethyl-2-methylpropane (7-FDA) and oxydipthalic anhydride (ODPA).

A 3-necked round bottom flask fitted with nitrogen inlet/outlet ports, a thermometer, and a magnetic stirring bar was charged with a solution of 1,3-diamino-2-heptafluorobutoxymethyl-2-methylpropane (2.1 g, 10 mmol) in dimethylacetamide (DMAC) (8 mL). The mixture was stirred at room temperature and ODPA (3.11 g, 10.03 mmol) was added under a positive nitrogen pressure. The resulting mixture was stirred at ambient temperature for 4 h. The resulting pale yellow, but clear, solution of polyamic acid was diluted with DMAC, spread on a glass plate and placed in an air oven at 80° C. for 16 h. Conversion of polyamic acid to polyimide was achieved thermally by heating the glass plate coated with polyamic acid in a nitrogen purged oven at 150° C. for 2 h, 200° C. for 1 h and at 325° C. for 1 h. The resulting polyimide film was continuous and adhered well to the glass. The plate was immersed in hot water to separate the yellow, but clear, fluorinated polyimide film from the glass plate. DSC analysis of the film did not reveal any transitions between room temperature and 350° C. The polyimide exhibited high thermal stability, with an onset of major thermal degradation in air occurring at 423° C.

EXAMPLE XXIII

This example illustrates the preparation and properties of a polyamide from 1,3-diamino-2-heptafluorobutoxymethyl-2-methylpropane (7-FDA) and adipoyl chloride.

A 50 mL, 3-necked round bottom flask fitted with a mechanical stirrer, thermometer, and argon purge was dried with a heat gun, cooled to room temperature under argon, and charged with a solution of 7-FDA (0,516 g, 1.72 mmol) in alcohol-free chloroform (5 mL). Next, a solution of adipoyl chloride (0.327 g, 1.78 mmol) in alcohol-free chloroform (3 mL) was added. An exotherm was observed. Next, triethylamine (0.27 mL, 0.196 g, 1.94 mmol) was added, and the mixture was stirred at room temperature for 4 days. The reaction mixture was washed with water (2×25 mL), dried over magnesium sulfate (MgSO$_4$), and filtered to give a solution of a polyamide in chloroform. This solution can be used to coat glass slides with a tack-free, clear film of the resulting fluorinated polyamide. Evaporation of the above solution yields an off-white, crystalline solid.

EXAMPLE XXIV

This example illustrates the preparation and properties of a transparent fluorinated polyurethane-urea elastomer.

A 3-necked, 25-mL round bottom flask fitted with a reflux condenser, nitrogen inlet/outlet ports, and a magnetic stirring bar was charged with poly-3-(2,2,3,3,4,4,4-heptafluorobutoxymethyl)-3-methyloxetane (poly-7-FOX) (5.002 g, 0.725 meq), IPDI (freshly distilled, 0.425 g, 3.82 meq), dibutyltin dilaurate (10 mg) and anhydrous tetrahydrofuran (10 mL). The mixture was heated under reflux for 4 h, cooled to room temperature, and slowly precipitated in hexane. The precipitated prepolymer is then washed with hexane (2×), redissolved in THF, and reprecipitated from 1,2-dichloroethane. The resulting oil was dried under reduced pressure (0.2 mm-Hg) at 60° C. for 16 h to give isocyanate-terminated poly-7-FOX, an amorphous oil. GPC analysis of the prepolymer reveal a unimodal molecular weight distribution with total absence of low molecular weight species such as IPDI: Mn=10,882(relative to polystyrene), Polydispersity=1.71; IR (neat film): 2270 (NCO), 1726 (C=O), and 1100–1250 (C-F) cm$^{-1}$. The equivalent weight of the prepolymer, as determined by titration (dibutylamine method), was 5,232. Isocyanate-terminated poly-7-FOX (1.0 g, 0.19) was then dissolved in anhydrous THF (1 mL) and reacted with 7-FDA (30 mg, 0.20 meq) at room temperature. The reaction mixture, a clear solution, was east in a petri dish and placed in a desiccator. Solvent was slowly evaporated over 2 days to give a void free film of the polymer. This film was then cured in an oven at 60° C. for 16 h to give a transparent, elastomeric, tack-free film of the tire polymer. The contact angle of this material with doubly distilled water was 108°, and the glass transition temperature as measured with DSC was –42° C.

The foregoing is offered primarily for purposes of illustration. It will be readily apparent to those of skill in the art that the operating conditions, materials, procedural steps and other parameters of the systems described herein may be further modified or substituted in various ways without departing from the spirit and scope of the present invention.

What is claimed is:

1. A compound having the formula:

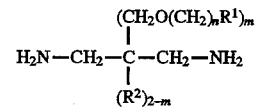

in which:

R$^1$ is selected from the group consisting of linear and branched chain perfluoroalkyls having from 1 to about 20 carbon atoms, omega-hydroperfluoroalkyls having from 1 to about 20 carbon atoms, and oxaperfluorinated polyethers having from 4 to about 60 carbon atoms;

R$^2$ is selected from the group consisting of lower alkyls having from 1 to 4 carbon atoms;

n is from 1 to about 10; and m is 1 or 2.

2. A compound in accordance with claim 1 wherein R$^1$ is a perfluoroalkyl selected from the group consisting of trifluoromethyl, pentafluoroethyl, heptafluoropropyl, tridecafluorohexyl, pentadecafluoroheptyl, heptadecafluorooctyl and heneicosafluorodecyl.

3. A compound in accordance with claim 1 wherein R$^2$ is a lower alkyl selected from the group consisting of methyl and ethyl.

4. A compound in accordance with claim 1 wherein R$^1$ is trifluoromethyl; R$^2$ is methyl; n is 1; and m is 1.

5. A compound in accordance with claim 1 wherein R$^1$ is trifluoromethyl; n is 1; and m is 2.

6. A compound in accordance with claim 1 wherein $R^1$ is pentafluoropropyl; $R^2$ is methyl; n is 1; and m is 1.

7. A compound in accordance with claim 1 wherein $R^1$ heptafluoropropyl; $R^2$ is methyl; n is 1; and m is 1.

8. A compound in accordance with claim 1 wherein $R^1$ is heptafluoropropyl; n is 1; and m is 2.

9. A compound in accordance with claim 1 wherein $R^1$ is tridecafluorohexyl; n is 2; and m is 2.

10. A compound in accordance with claim 1 wherein $R^1$ is tridecafluorohexyl; $R^2$ is methyl; n is 2; and m is 1.

11. A compound in accordance with claim 1 wherein $R^1$ is pentadecafluoroheptyl; $R^2$ is methyl; n is 1; and m is 1.

12. A compound in accordance with claim 1 wherein $R^1$ is heptadecafluorooctyl; $R^2$ is methyl; n is 2; and m is 1.

13. A compound in accordance with claim 1 wherein $R^1$ is heneicosafluorodecyl; $R^2$ is methyl; n is 2; and m is 1.

14. A compound in accordance with claim 1 wherein $R^1$ is a mixture of trifluorohexyl, heptadecafluorooctyl and heneicosafluorodecyl; $R^2$ is methyl; n is 2; and m is 1.

15. A compound in accordance with claim 1 wherein $R^1$ is a mixture of trifluorohexyl, heptadecafluorooctyl and heneicosafluorodecyl; n is 2; and m is 2.

* * * * *